US012599138B2

(12) United States Patent
Hillyer et al.

(10) Patent No.: US 12,599,138 B2
(45) Date of Patent: Apr. 14, 2026

(54) CELLULOSIC FIBERS COMPRISING INTERNALLY DISPERSED CUPROUS OXIDE NANOPARTICLES

(71) Applicant: The United States of America, as represented by the Secretary of Agriculture, Washington, DC (US)

(72) Inventors: Matthew B Hillyer, New Orleans, LA (US); Sunghyun Nam, Metairie, LA (US); Brian D Condon, Metairie, LA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 273 days.

(21) Appl. No.: 17/371,906

(22) Filed: Jul. 9, 2021

(65) Prior Publication Data

US 2023/0011248 A1     Jan. 12, 2023

(51) Int. Cl.

| | |
|---|---|
| *A01N 59/20* | (2006.01) |
| *A01N 25/34* | (2006.01) |
| *A23B 4/20* | (2006.01) |
| *A23B 4/24* | (2006.01) |
| *A61L 2/232* | (2006.01) |
| *A61L 9/012* | (2006.01) |
| *B65D 65/42* | (2006.01) |
| *B65D 81/28* | (2006.01) |
| *D06M 11/42* | (2006.01) |
| *A61L 101/26* | (2006.01) |
| *D06M 101/06* | (2006.01) |

(52) U.S. Cl.
CPC ............. *A01N 59/20* (2013.01); *A01N 25/34* (2013.01); *A23B 4/20* (2013.01); *A23B 4/24* (2013.01); *A61L 2/232* (2013.01); *A61L 9/012* (2013.01); *B65D 65/42* (2013.01); *B65D 81/28* (2013.01); *D06M 11/42* (2013.01); *A23V 2002/00* (2013.01); *A61L 2101/26* (2020.08); *A61L 2202/26* (2013.01); *D06M 2101/06* (2013.01)

(58) Field of Classification Search
CPC .......... A01N 59/20; A01N 25/34; A23B 4/20; A23B 4/24; A61L 2/232; A61L 9/012; A61L 2101/26; A61L 2202/26; B65D 65/42; B65D 81/28; D06M 11/42; D06M 2101/06; D06M 16/00; D06M 23/08; A23V 2002/00; A01P 1/00
See application file for complete search history.

(56) References Cited

U.S. PATENT DOCUMENTS

| | | | |
|---|---|---|---|
| 5,049,159 A | | 9/1991 | Yamaji et al. |
| 2014/0302336 A1* | | 10/2014 | Heiskanen ............... D21C 9/00 106/204.3 |
| 2015/0336804 A1 | | 11/2015 | Dankovich |

FOREIGN PATENT DOCUMENTS

| | | | |
|---|---|---|---|
| CN | 107140673 A | | 9/2017 |
| CN | 112626842 A | | 4/2021 |
| JP | 2017008449 A | | 1/2017 |
| JP | 2017088509 A | * | 5/2017 |
| WO | 2017124057 A1 | | 7/2017 |

OTHER PUBLICATIONS

Radetic, M.; Markovic, D. Nano-finishing of cellulose textile materials with copper and copper oxide nanoparticles. Review Paper. Cellulose, 26: 8971-8991. (Year: 2019).*
Boylston, E. et al., 1991, "A quick embedding method for light and electron microscopy of textile fibers," Biotech. Histochem. 66 (3): 122-124.
Da Costa W.V., et al., 2017, "Hybrid materials based on cotton fabric-Cu2O nanoparticles with antibacterial properties against *S. aureus*," Materials Chemistry and Physics 201: 339-343.
Errokh A., et al., 2016, "Controlled growth of Cu2O nanoparticles bound to cotton fibres," Carbohydrate Polymers 141: 229-237.
Gardner K.H. and Blackwell J, 1974, "The structure of native cellulose," Biopolymers 13(10): 1975-2001.
Gouda M., et al., 2015, "Preparation and Characterization of Some Nanometal Oxides Using Microwave Technique and Their Application to Cotton Fabrics," J. Nanomater. 2015:1-9. doi: 10.1155/2015/586904.
Hage, J.L.T., et al., 1999, "Reduction of copper with cellulose in an autoclave; an alternative to electrolysis?" Miner. Eng. 12 (4):393-404. doi:10.1016/s0892-6875(99)00019-9.
Lee H-J., et al., 2011, "Biological synthesis of copper nanoparticles using plant extract," Nanotechnology 1(1):373-374.
Sarko A. and Muggli R., 1974, "Packing analysis of carbohydrates and polysaccharides. III. Valonia cellulose and cellulose II," Macromolecules 7(4): 486-494.
Sedighi A., et al., 2014, "Synthesis of nano Cu2O in cotton: Morphological, physical, biological and optical sensing characterizations," Carbohydrate Polymers 110: 489-498.
Sharma P., et al., 2019, "Green synthesis and characterization of copper nanoparticles by Tinospora cardifolia to produce nature-friendly copper nano-coated fabric and their antimicrobial evaluation," J. Microbiol. Methods 160:107-116; doi:10.1016/j.mimet.2019.03.007.

(Continued)

*Primary Examiner* — Jessica Worsham
(74) *Attorney, Agent, or Firm* — John Fado; Maria Restrepo-Hartwig

(57) ABSTRACT

The invention relates to treated cellulosic fibers comprising internally dispersed cuprous oxide (Cu₂O) nanoparticles, methods of preparing such treated cellulosic fibers, and uses of such treated cellulosic fibers.

19 Claims, 12 Drawing Sheets

(56)        References Cited

OTHER PUBLICATIONS

Thibodeaux, D. P. and Evans, J. P., 1986, "Cotton fiber maturity by image analysis," Text. Res. J. 56: 130-139.

Tran TH and Nguyen VT, 2014, "Copper Oxide Nanomaterials Prepared by Solution Methods, Some Properties, and Potential Applications: A Brief Review," International Scholarly Research Notes, vol. 2014, Article ID 856592.

Xiong J. et al., 2011, "Synthesis of highly stable dispersions of nanosized copper particles using L-ascorbic acid," Green Chem. 13: 900.

Yang L., et al., 2021, "Controllable fabrication and self-assembly of Cu nanostructures: the role of Cu2+ complexes," RSC Adv. 11: 17715-17720.

International Search Report on PCT/US2022/036226 dated Nov. 1, 2022.

International Searching Authority Written Opinion on PCT/US2022/036226 dated Nov. 1, 2022.

\* cited by examiner

FIG. 1

$$Cu^{II}SO_4 \xrightarrow{\text{NaOH}} Cu^{II}(OH)_2 \xrightarrow{\text{excess NaOH}} [Cu^{II}(OH)_4]^{2-} + NaOH$$

oxidized cellulose

FIG. 4A        FIG. 4B

Binding Energy (eV)

Binding Energy (eV)

Feret Diameter (nm)

Feret Diameter (nm)

FIG. 12A　　　　　　　　FIG. 12B
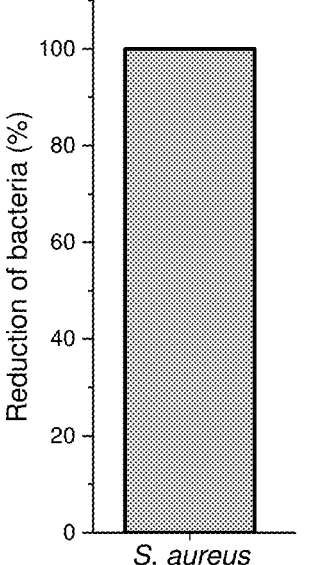
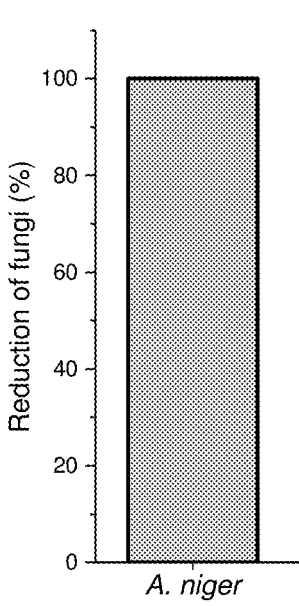

CELLULOSIC FIBERS COMPRISING INTERNALLY DISPERSED CUPROUS OXIDE NANOPARTICLES

FIELD OF THE INVENTION

The invention relates to cellulosic fibers comprising internally dispersed cuprous oxide ($Cu_2O$) nanoparticles, methods of preparing such cellulosic fibers, and uses of such cellulosic fibers.

BACKGROUND OF THE INVENTION

Metal and metal oxide nanomaterials exhibit remarkable physical, chemical, and optical properties due to their nanoscopic size and high surface area-to-volume ratio that are unique and different than their corresponding bulk materials. These include silver, gold, palladium, platinum, chromium, ruthenium, manganese, zinc, nickel, zirconium, cobalt, iron, and copper. Particularly, the versatile and cost-effectiveness of copper has guided researchers toward investigating the application of copper and its oxide nanomaterials in catalysis, gas-phase sensing, electrochemistry, energy production and storage, and pharmaceuticals. Due to the utility of these nanomaterials they have also found use in commercial products such as agrochemicals, cosmetics, paints, foods, medical devices, and antimicrobial agents. The textile industry frequently employs copper and copper oxide nanoparticles ($Cu_xONPs$, where x=1 or 2) to imbue dye fastness, UV-protection, and antibacterial activity to cotton fibers.

While synthetic fibers have become popular in recent years, there has been a market trend towards increased use of cotton for commercial textiles. Laundering and disposal of synthetic fibers lead to the release of microplastics into water supplies and ecosystems. Many recent studies have revealed the ecotoxicological impacts these microplastics have had on human health, and on fish, plants, and microorganisms in aquatic ecosystems. Cotton is an eco-friendly and sustainable alternative to synthetic fibers. Additionally, cotton is durable, a great insulator, and retains moisture far more effectively than synthetic fibers, finding utility in many personal and medical textile products. However, due to its hygroscopicity cotton fibers are susceptible to damage by microorganisms, which can lead to a myriad of negative health effects in humans. For this reason, copper and copper oxide nanomaterials have been used as antimicrobial coatings, imparting resistance to microorganism growth. Antibacterial experiments comparing the oxidation state of copper suggest that nanomaterials containing metallic copper (0)—and copper (I)—are the most microbicidal, followed by those containing copper (II).

There are many methods available for synthesizing $Cu_x$-ONPs, such as sol-gel, laser ablation, sonochemical, electrochemical reduction, coprecipitation, biological, microwave irradiation, etc. Many of these synthetic methods are simple and high-yielding, however, they require toxic reducing agents and are energy demanding. $Cu_xONPs$ are prepared and subsequently applied to cotton fibers by either dip-pad-dry or by using chemical binding agents. To this end, the externally applied $Cu_xONPs$ can be easily detached during use and laundering, which has led to concerns regarding the potential environmental impacts.

Thus, a method to prepare internally-dispersed cuprous oxide nanoparticles in cotton without the use of reducing agents is needed.

SUMMARY OF THE INVENTION

Provided herein are cellulosic fibers comprising internally dispersed cuprous oxide ($Cu_2O$) nanoparticles, methods for preparing such cellulosic fibers, and uses for such cellulosic fibers.

In an embodiment, the invention relates to a treated cellulosic fiber comprising internally dispersed cuprous oxide nanoparticles. In some embodiments of the invention, the treated cellulosic fiber comprising internally dispersed cuprous oxide nanoparticles is from cotton, flax, hemp, jute, ramie, pineapple leaf, or abaca. In some embodiments of the invention, the treated cotton fiber comprising internally dispersed cuprous oxide nanoparticles is greige cotton, scoured cotton, or scoured and bleached cotton.

In some embodiments, the invention relates to a treated cellulosic fiber comprising internally dispersed cuprous oxide nanoparticles, where the internally dispersed cuprous oxide nanoparticles have a median Feret diameter of about 5 mm to about 100 mm. In some embodiments of the invention the concentration of internally dispersed cuprous oxide nanoparticles in the treated cellulosic fiber comprising internally dispersed cuprous oxide nanoparticles is at least about 0.001 mg/kg.

In some embodiments of the invention, at least about 20% of the cuprous oxide nanoparticles remain internally dispersed in the treated fiber after at least about 5 laundering cycles. In some embodiments of the invention, the treated cellulosic fiber comprising internally dispersed cuprous oxide nanoparticles inhibits at least one of odor, microbial growth, bacterial growth, viral growth, or fungal growth. In some embodiments of the invention, the treated cellulosic fiber comprising internally dispersed cuprous oxide nanoparticles inhibits odor, microbial growth, bacterial growth, viral growth, and fungal growth.

In an embodiment, the invention relates to an article comprising at least one cellulosic fiber comprising internally dispersed cuprous oxide nanoparticles. In some embodiments of the invention, the article comprising at least one cellulosic fiber comprising internally dispersed cuprous oxide nanoparticles is at least one of antimicrobial, antibacterial, anti-odor, anti-viral, or anti-fungal. In some embodiments of the invention, the article comprising at least one cellulosic fiber comprising internally dispersed cuprous oxide nanoparticles is yarn, a thread, a twine, a rope, a cloth, a woven fabric, a knitted fabric, a film-based composite, a nonwoven fabric, or a final article. In some embodiments of the invention, the final article comprising at least one cellulosic fiber comprising internally dispersed cuprous oxide nanoparticles comprises all or part of athletic wear, an undergarment, military wear, a medical textile, or a functional barrier. In some embodiments of the invention, the medical textile comprising at least one cellulosic fiber comprising internally dispersed cuprous oxide nanoparticles is a curtain, a bedding, a surgical arena fabric, a personnel protective garment, a wound or non-wound patient dressing, a bandage, a gauze, a packing, or a cleaning material. In some embodiments of the invention, the final article comprising at least one cellulosic fiber comprising internally dispersed cuprous oxide nanoparticles is all or part of an antimicrobial packaging. In some embodiments of the invention, the medical textile comprising at least one cellulosic fiber comprising internally dispersed cuprous oxide nanoparticles is a curtain, a bedding, a surgical arena fabric, a surgical personnel protective garment, a wound or non-wound patient dressing, a bandage, a gauze, a packing, or a cleaning material.

In an embodiment, the invention relates to a final article that is all or part of an antimicrobial, antibacterial, anti-odor, anti-viral, or anti-fungal packaging. In some embodiments of the invention, the antimicrobial, antibacterial, anti-odor, anti-viral, or anti-fungal packaging is an agricultural or food packaging.

In an embodiment, the invention relates to a method for preparing a treated cellulosic fiber comprising internally dispersed cuprous oxide nanoparticles. The method comprises immersing a cellulosic fiber in a solution comprising a copper (II) precursor and a base to prepare a copper complex $[Cu(OH)_4]^{2-}$ that diffuses through the interior of the cellulosic fiber; transferring the cellulosic fiber with the diffused copper complex $[Cu(OH)_4]^{2-}$ to water to produce a cellulosic fiber comprising $Cu(OH)_2$; and allowing the $Cu(OH)_2$ cellulosic fiber to dry, thus preparing a treated cellulosic fiber comprising internally dispersed cuprous oxide nanoparticles. In some embodiments of the invention, the water to which the cellulosic fiber with the diffused copper complex $[Cu(OH)_4]^{2-}$ is transferred is at about room temperature (about 23° C.).

In some embodiments of the invention, the copper (II) precursor into which the cellulosic fiber is immersed to prepare a treated cellulosic fiber comprising internally dispersed cuprous oxide nanoparticles is copper (II) sulfate, copper 2-ethylhexanoate, copper acetate triarsenite, copper acetate, copper acetylacetonate, copper acetylide, copper arsenate, copper arsenite, copper aspirinate, copper azide, copper benzoate, copper bromide, copper carbonate, copper carbonate hydroxide, copper chlorate, copper chloride, copper chromate, copper chromite, copper cyanide, copper cyanurate, copper cyclohexanebutyrate, copper fluoride, copper gluconate, copper glycinate, copper hexafluoroacetylacetonate, copper hydride, copper hydroxide, copper iodide, copper nitrate, copper nitrite, copper oxide, copper perchlorate, copper peroxide, copper phosphate, copper phosphide, copper pyrophosphate, copper selenite, copper sulfate pentahydrate, copper sulfate, copper sulfide, copper tartrate, copper t-butoxide, copper tetraamine, copper tetrafluoroborate, copper thiocyanate, copper thiophene-2-carboxylate, copper triflate, copper trifluoroacetate, copper trifluoroacetylacetonate, copper usnate, or a hydrate thereof. In some embodiments of the invention, the base into which the cellulosic fiber is immersed to prepare a treated cellulosic fiber comprising internally dispersed cuprous oxide nanoparticles is a hydroxide, a carbonate, or other organic base or inorganic base.

In an embodiment, the invention relates to a treated cellulosic fiber comprising internally dispersed cuprous oxide nanoparticles prepared by the methods taught here.

BRIEF DESCRIPTION OF THE DRAWINGS

FIG. 1 depicts a reaction schematic for the internal synthesis of cuprous oxide nanoparticles in cotton.

FIG. 3A shows an image taken at 2000× magnification. FIG. 3B shows an image taken at 20000× magnification. FIG. 3C shows an image taken at 50000× magnification. The white outline in FIG. 3A and FIG. 3B represents the area of magnification.

FIG. 4A to FIG. 4C depict the FE-SEM image, EDS mapping for Cu element, and a graph of the EDS spectrum graph for treated cotton fiber. FIG. 4A shows the FE-SEM image; FIG. 4B shows the EDS mapping for Cu element; FIG. 4C shows a graph of the EDS spectrum for a point on the surface of the treated cotton fabric. The Y axis displays the counts and the X axis displays the energy in kilo electron volts (keV). The different peaks are labeled.

FIG. 5A shows a graph of the XRD pattern of untreated cotton fabric. FIG. 5B shows a graph of the XRD pattern of $Cu_2ONP$-cotton fabric. The Y axis displays amount of counts per minute; the X axis displays the 2 theta angle (2θ).

FIG. 6A shows a graph of the full XPS spectrum, with the O1s and C1s regions indicated. FIG. 6B shows a graph of the XPS spectrum focused on the $Cu_2O$ peaks. The Y axis displays the relative intensity in absorbance units (A.U.); the X axis displays the Binding Energy in electron volts (eV). The position of the $Cu2p_{1/2}$, $Cu2p_{3/2}$, and weak satellite peaks are indicated/

FIG. 7A presents an image of the edge and interior of a $Cu_2ONP$-cotton fiber. FIG. 7B presents a 2× magnification of the image in FIG. 7A. FIG. 7C presents a 4× magnification of the image in FIG. 7A.

FIG. 8A shows a graph of the cumulative percent of the mean Feret diameters of the $Cu_2ONPs$ formed in the cotton fiber. The Y axis displays the cumulative percent for each size. FIG. 8B shows the number of particles of the mean Feret diameters of the $Cu_2ONPs$ formed in the cotton fiber. The Y axis displays the number of particles. In both figures, the X axis displays the Feret diameter in nanometers (nm).

FIG. 9A presents a graph of the UV-vis spectra of increasing copper concentrations in $Cu_2ONP$-cotton. The Y axis displays the relative absorbance units (A.U.). The X axis displays the wavelength in nm. Solid line shows the data for 17,489 ppm; long dash line shows the data for 9,213 ppm; dotted line shows the data for 5,554 ppm; dash-dot line shows the data for 1,289 ppm; dash-dot-dot line shows the data for 667 ppm; short dash line shows data for 344 ppm; and dotted line shows data for 0 ppm. FIG. 9B presents a graph of the calibration curve of SPR intensity at 320 nm vs. ICP-MS determined copper concentration. The Y axis displays the copper concentration in ppm. The X axis displays the relative absorbance units.

FIG. 11A presents the remaining copper content measured using ICP-MS. FIG. 11B presents the remaining copper content measured using UV-vis. Y axis shows the calculated percent copper concentration; X axis shows the number of laundering cycles.

FIG. 12A and FIG. 12B depict graphs of the reduction of bacteria or fungi by $Cu_2ONP$-cotton fabrics after undergoing 50 laundering cycles. FIG. 12A shows a graph of the reduction in *S. aureus* growth after 24 hours exposure. FIG. 12B shows a graph of the reduction in *A. niger* growth after 24 hours exposure.

DETAILED DESCRIPTION

Figure 2:
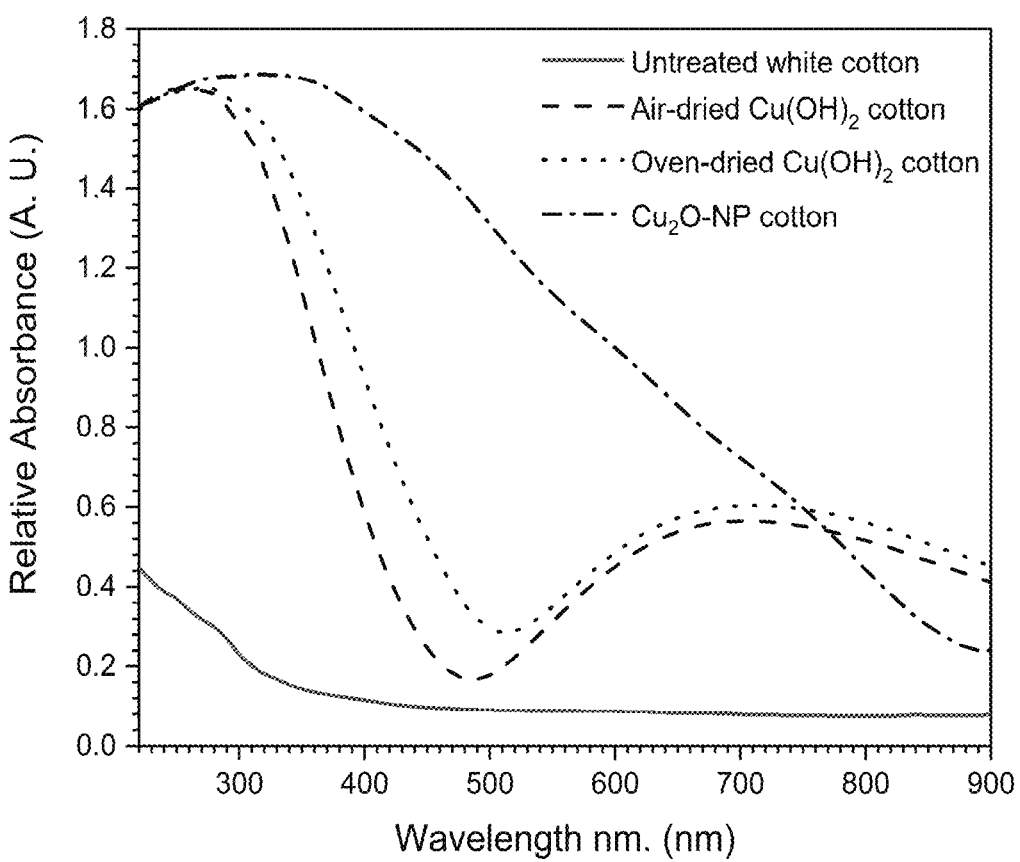
FIG. 2 depicts a graph of the UV-vis absorbance spectra of untreated fabric, air-dried $Cu(OH)_2$-incorporated fabric, oven-dried $Cu(OH)_2$-incorporated fabric, and $Cu_2ONP$-cotton fabric. The Y axis presents the relative absorbance in absorbance units (AU); the X axis presents the wavelength in nm. Solid line, untreated white cotton; dashed line, air dried $Cu(OH)_2$ cotton; dotted line, oven-dried $Cu(OH)_2$ cotton; dash-dot line $Cu_2ONP$ cotton.

The inventors have developed a method of forming cuprous oxide nanoparticles internally dispersed in cellulosic fibers without the use of reducing agents. The $Cu_2ONPs$ formed by the method of the invention remain internally dispersed in the cellulosic fibers even after many laundering cycles. The internally-dispersed $Cu_2ONPs$ impart anti-bacterial, anti-fungal, and anti-viral properties to cellulosic fibers.

Current methods for incorporating antibacterial metal oxide nanoparticles in textiles and packaging materials use a surface adsorption method to functionalize nanomaterials to fibers. However, this results in poor durability and decreased antimicrobial activity after consecutive launderings of the textiles and packaging materials. Cotton fabrics with multifunctional properties infused with metal oxide nanoparticles for antibacterial applications are becoming increasingly popular. Copper oxide nanomaterials have gained popularity for their synthetic versatility, microbicidal properties, and cost-effectiveness compared to nanomaterials from other metals.

The inventors developed a method for in situ development of internally dispersed cuprous oxide nanoparticles in cellulosic fibers. These cuprous oxide nanoparticles are synthesized in situ from a copper (II) precursor under mild conditions and without the addition of reducing agents or binders. Any common copper II precursor may be used in the methods of the invention for forming internally dispersed cuprous oxide nanoparticles in treated cellulosic fibers. Examples of copper II precursors that may be used to create cuprous oxide nanoparticles in a cellulosic fiber are, for example, copper (II) sulfate, copper 2-ethylhexanoate, copper acetate triarsenite, copper acetate, copper acetylacetonate, copper acetylide, copper arsenate, copper arsenite, copper aspirinate, copper azide, copper benzoate, copper bromide, copper carbonate, copper carbonate hydroxide, copper chlorate, copper chloride, copper chromate, copper chromite, copper cyanide, copper cyanurate, copper cyclohexanebutyrate, copper fluoride, copper gluconate, copper glycinate, copper hexafluoroacetylacetonate, copper hydride, copper hydroxide, copper iodide, copper nitrate, copper nitrite, copper oxide, copper perchlorate, copper peroxide, copper phosphate, copper phosphide, copper pyrophosphate, copper selenite, copper sulfate pentahydrate, copper sulfate, copper sulfide, copper tartrate, copper t-butoxide, copper tetraamine, copper tetrafluoroborate, copper thiocyanate, copper thiophene-2-carboxylate, copper triflate, copper trifluoroacetate, copper trifluoroacetylacetonate, copper usnate, or a hydrate thereof.

The method for in situ development of internally dispersed cuprous oxide nanoparticles in cellulosic fibers requires the use of a base such as a hydroxide, a carbonate, or other organic base or inorganic base. Inorganic bases useful for the in situ development of internally dispersed cuprous oxide nanoparticles in cellulosic fibers may be an alkali hydroxide, an alkaline earth hydroxide, a transition metal hydroxide, a metal hydroxide, an alkali carbonate, an alkaline earth carbonate, a transition metal carbonate, a metal carbonate, an alkali acetate, an alkaline earth acetate, a transition metal acetate, a metal acetate, an alkali amide, an alkaline earth amide, a transition metal amide, a metal amide, an alkali oxalate, an alkaline earth oxalate, a transition metal oxalate, or a metal oxalate. Organic bases useful for the in situ development of internally dispersed cuprous oxide nanoparticles in cellulosic fibers may be ammonia, pyridine, 1,4-diazabicyclo[2.2.2]octane, 1,8-diazabicyclo[5.4.0]undec-7-ene, 1,5-diazabicyclo[4.3.0]non-5-ene, 1,5,7-triazabicyclo[4.4.0]dec-5-ene, methylamine, dimethylamine, trimethylamine, ethylamine, diethylamine, triethylamine, 4-(dimethylamino)pyridine, 2,6-lutidine, piperidine, tert-butoxides, ethoxides, methoxides, tetraalkylammonium hydroxides, tetraalkylammonium carbonates, tetraalkylammonium acetates, tetraalkylammonium amides, tetraalkylammonium oxalates.

Figure 1:
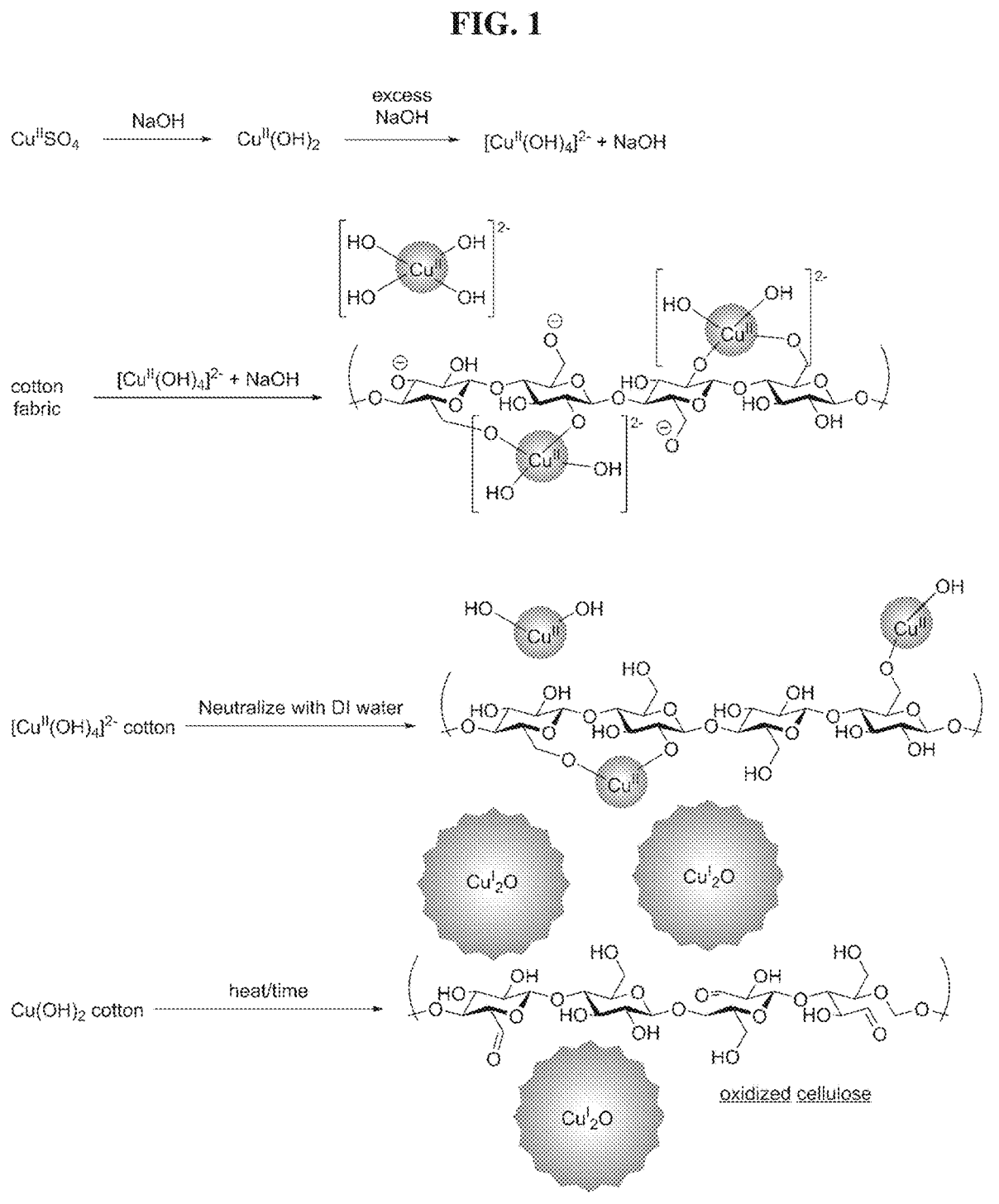

FIG. 1 depicts a reaction schematic for the internal synthesis of cuprous oxide nanoparticles in cotton. As seen in this figure, addition of sodium hydroxide to a copper sulfate solution precipitated insoluble copper hydroxide complex ($Cu(OH)_2$). Further addition of sodium hydroxide caused the formation of cuprate salt ($Cu(OH)_4^{2-}$). Without wishing to be bound by theory, it is believed that when cotton fabric was immersed in the cuprate salt, the excess hydroxide present in the highly alkaline $Cu(OH)_4^{2-}$ solution deprotonated the hydroxides of the cellulose backbone, and the 4-coordinate copper center strongly associated with the closely-packed alkoxides of the deprotonated cellulose chains. The light blue color of the fabric changed to a darker blue color, an indication of the cuprate salt ions binding to the cellulose. As the cotton fabric was rinsed with deionized (DI) water, the treated cotton fabric changed from dark blue to light blue. Similarly, without wishing to be bound by theory, it is believed that this change correlated with the transition from a $Cu(OH)_4^{2-}$ to $Cu(OH)_2$, and the $Cu^{II}$ ions remained bound to the deprotonated hydroxides in the interior of the microfibrillar structure of cotton. Subsequent addition of the fabric to water gave a brown fabric where it is believed that cuprous oxide nanoparticles were formed and dispersed internally in the fibers.

In an embodiment, the invention relates to treated cellulosic fiber comprising internally dispersed cuprous oxide nanoparticles. Treated cellulosic fibers with internally dispersed cuprous oxide nanoparticles may be prepared by any available cellulosic fiber. In some embodiments of the invention the cellulosic fiber treated to form internally dispersed cuprous oxide nanoparticles is cotton, flax, hemp, jute, ramie, pineapple leaf, or abaca. In some embodiments of the invention, the cellulosic fiber treated to form internally dispersed cuprous oxide nanoparticles is scoured and bleached cotton fiber, white cotton fiber, naturally colored cotton fiber, or greige cotton fiber.

Cotton is unique among crop plants in that it produces seed trichomes, or fibers, that consist of extremely elongated single cells. Four separate cotton species have been domesticated independently. *Gossypium hirsutum* and *G. barbadense* are cotton species from the Americas, and *G. arboretum* and *G. herbaceum* are from Africa-Asia. At least five major types of cotton are currently grown commercially around the world: American upland, Egyptian, Sea-Island, Asiatic, and American Pima. The various kinds of cotton plants resemble each other in most ways, but they differ in such characteristics as color of flowers, character of fibers, and time of blooming. In addition, each main type has varieties with different characteristics, for example, some varieties grow best on irrigated land, the fibers produced by some of the cotton types are about one and three quarter inches long, while the fibers produced by other cotton types are only about half an inch long, and the fibers produced by some cotton varieties are stronger than the fibers produced other cotton varieties.

Each cotton fiber is a single cell with a multilayer structure. Under the microscope, a cotton fiber looks like a very fine, twisted ribbon, or a collapsed and twisted tube. The seed end of the fiber is quite irregular, having been torn during ginning from the epidermis or skin of the cotton seed. Cotton fibers are easily visible to the naked eye, and may be anywhere from about half an inch (1.27 cm) to about two and three quarter inches (6.985 cm) in length, and from about 11 μm to about 22 μm in diameter. Cellulose is a major component of the cell walls that surround all plant cells. Cotton fibers may be thought as the dried out remains of extraordinarily long and thick cell walls. The cotton fibers are mostly made of cellulose, a macromolecule made up of anhydroglucose units connected by 1, 4 oxygen bridges with the polymer repeating unit being anhydro-beta-cellulose. Cotton cellulose has higher degrees of polymerization and crystallinity than wood and rayon cellulose. Higher degrees of polymerization and crystallinity of polymers are associated with higher strengths. Fibers from domesticated cotton are the longest cells of any plant. A cotton fiber cross-section is oval, and from the outside of the fiber to the inside, the layers in a mature cotton fiber cell are cuticle, primary wall, winding or transition layer, secondary wall, and lumen. The cuticle is the outer layer of a cotton fiber, is a few molecules thick, and contains various non-cellulosic components such as pectin, proteins, sugars, and wax. Scouring removes the dirt and grease that cotton fibers accumulate during manufacturing and transit. The cuticle is removed from the cotton fiber during the scouring process. The primary wall is the original thin cell wall. Each cell wall consists of microfibrils, which are randomly aligned in the winding layer and the primary wall, and are unidirectionally aligned at different angles to the fiber axis in the secondary wall. The size of typical cellulosic microfibrils ranges from about ten to about twenty nm in width, with an average aspect ratio of about twenty to one hundred. The lumen is the hollow space in the center of the fiber. The lumen is initially filled with living protoplast, which dries out when the fiber matures.

The internal structure of cotton fiber greatly swells in a concentrated alkaline solution, causing irreversible changes in the characteristics of the cotton fiber, e.g., uncoiling of the twisted ribbon-like fiber shape into a smoother rounder shape. Moreover, under alkaline treatment, the crystalline structure is altered from cellulose Iβ to cellulose II (Gardner K. H. and Blackwell J, 1974, "*The structure of native cellulose,*" Biopolymers 13(10): 1975-2001; Sarko A. and Muggli R., 1974, "*Packing analysis of carbohydrates and polysaccharides. III. Valonia cellulose and cellulose II,*" Macromolecules 7(4): 486-494). This alkaline treatment, called mercerization, has traditionally been conducted to enhance the luster, strength, and dye affinity of cotton fiber. Using the methods of the invention, internally dispersed cuprous oxide nanoparticles were obtained by treating mercerized or non-mercerized cotton fibers with a copper (II) precursor under mild conditions and without the addition of reducing agents or binders.

American Upland Cotton is the type of white cotton most commonly cultivated in the South and Southwest of the United States of America. It constitutes about 95% of all cotton produced in the United States. The American Upland Cotton has short to medium staple fibers.

White cotton fiber is commonly scoured and bleached. Scouring removes natural hydrophobic components such as oil and wax from the surface of the fiber, improving the efficiency of bleaching, dyeing, and finishing processes. Bleaching removes the natural pigment from cotton fiber. Most, or all, of the non-cellulosic components are removed from raw cotton fiber that has been scoured and bleached. Cellulose is a reducing agent, and when using the methods of the invention to prepare cellulosic fibers with internally dispersed cuprous oxide nanoparticles, cotton cellulose reduces copper (II) ions to copper (I). Reducing agents are required for the reduction reaction in a typical nanoparticle synthesis. In the instant methods, the cellulose acts as the reducing agent. Thus, there is no need to add additive reducing agents to the method of forming internally dispersed cuprous oxide nanoparticles in the treated cellulosic fibers of the invention. Following the methods of the invention, the internal structure of the cotton fiber stabilizes the growth of the nanoparticles. In a typical nanoparticle synthesis stabilizing agents are required to control the particle growth. In the instant methods, the cellulose fiber acts as the stabilizing agent. Thus, there is no need to add additive stabilizing agents to the method of forming internally dispersed cuprous oxide nanoparticles in the treated cellulosic fibers of the invention.

Hemp, flax, kenaf, jute, and ramie are bast fiber plants. Bast fibers are long, narrow supportive cells inside the phloem that provide it with great tensile strength, but still allow flexibility of the plant stem due to the fibers' characteristic fiber nodes, or weak points that are distributed randomly along the length of the fiber. These fiber nodes are also what make fabric made from bast fiber flexible without being brittle. Flax (*Linum usitatissimum*) is an herbaceous annual plant of the Linaceae family, which is cultivated for its fiber and for its nutritious seeds, from which linseed oil is obtained. Linen yarn and fabric are made from flax fiber, which according to historical records, is one of the oldest known textile fibers. Flax fiber is a natural, cellulosic, multi-cellular bast fiber, and is obtained from the inner bark of the stem of the flax plant. Flax fiber is about 10 to about 100 cm in length, and its diameter varies from about 40 to about 80 μm. Flax fiber is stronger than cotton fiber as its polymers lie almost parallel to the fiber axis. The fiber strands are made up of individual cylindrically-shaped cells with fairly smooth surfaces. Flax fiber varies in color from creamy white to gray. Hemp is also one of the bast fibers known to ancient Asians. The fibers in kenaf are found in the bast (bark) and core (wood). The bast constitutes 40% of the plant. "Crude fiber" separated from the bast is multi-cellular, consisting of several individual cells stuck together. Jute is a strong, coarse fiber used for making burlap, gunny, cordage, etc., obtained from two East Indian plants, *Corchorus capsularis* and *C. olitorius*, of the linden family. Ramie has been used for several thousand years in China. The ramie plant is a tall perennial shrub from the nettle family that requires a hot, humid climate for growth. Ramie fiber is longer than 150 cm.

Bast fiber is obtained by subjecting the stalks to a series of operations, including retting (the use of moisture and microorganisms to dissolve the tissues surrounding the fibers), drying, crushing, and beating.

In an embodiment of the invention, the treated cellulosic fiber comprising internally dispersed cuprous oxide nanoparticles is from cotton, flax, hemp, jute, ramie, pineapple leaf, or abaca. In some embodiments, the invention relates to treated cotton fiber comprising internally dispersed cuprous oxide nanoparticles, where the cotton is greige cotton, scoured cotton, or scoured and bleached cotton. In some aspects of the invention, the cotton in the treated cotton fiber comprising internally dispersed cuprous oxide nanoparticles is white cotton or naturally colored cotton.

The inventors have devised a method for the in situ synthesis of copper (I) oxide nanoparticles within cellulosic fibers from a copper (II) precursor under mild conditions, without adding a reducing or binding agent The in situ synthesis taught herein resulted in the internal formation of cuprous oxide nanoparticles dispersed within the cotton fiber. In some embodiments, the invention relates to treated cellulosic fiber from cotton, flax, hemp, jute, ramie, pineapple leaf, or abaca comprising internally dispersed cuprous oxide nanoparticles. In some embodiments of the invention, the cellulosic fiber with internally dispersed cuprous oxide nanoparticles in greige cotton, white cotton, naturally colored cotton, scoured cotton, or scoured and bleached cotton.

A variety of techniques including UV-vis spectroscopy, X-ray diffraction (XRD), X-ray photoelectron spectroscopy (XPS), energy-dispersive X-ray (EDS) spectroscopy, transmission electron microscopy (TEM), and field emission scanning electron microscopy (FE-SEM) were used to determine the morphology and composition of the $Cu_2ONPs$ produced on the surface and within the cotton fibers. As seen in FIG. 2, the relative UV-vis absorbance of treated cellulosic fabric rinsed with DI water and either air dried or oven dried gave an increase in relative absorbance at 290 nm, with a second peak at 713 nm. Not wishing to be bound by theory, it is believed that the $Cu(OH)_2$ inside the fabric was very stable when the fabric was dried because little change was observed when the fabric was heated in an oven to 150° C. for several hours. As the neutralized treated cotton fabric was immersed in an 80° C. water bath the color of the fabric changed immediately to a dark brown color. The UV-vis spectrum for the brown cotton fabric showed a peak at 320 nm, which corresponds to the surface plasmon resonance of the newly formed copper (I) oxide ($Cu_2O$).

Figure 3A:
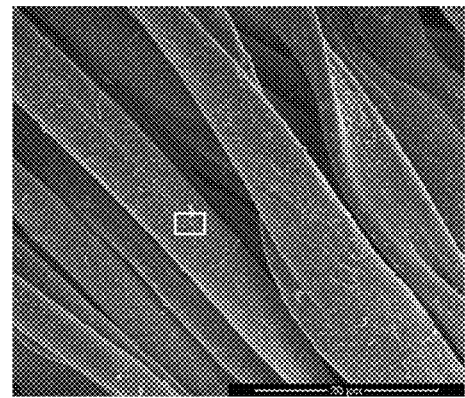
FIG. 3A to 3C depict Field Emission Scanning Electron Microscopy (FE-SEM) images of the cuprous oxide nanoparticles ($Cu_2ONPs$) produced on the surface of cotton fibers.
Figure 3B:
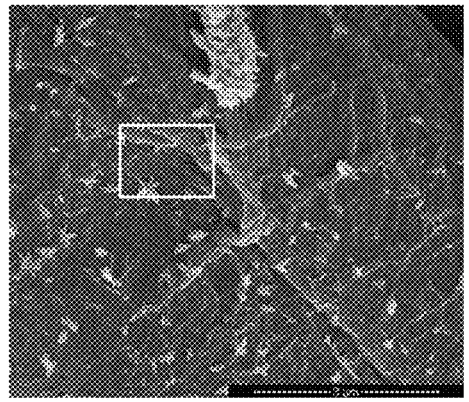
Figure 3C:
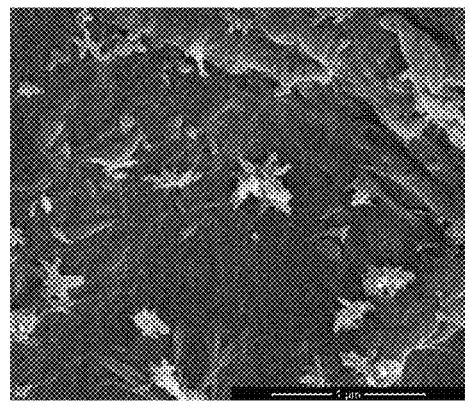
Figure 4C:
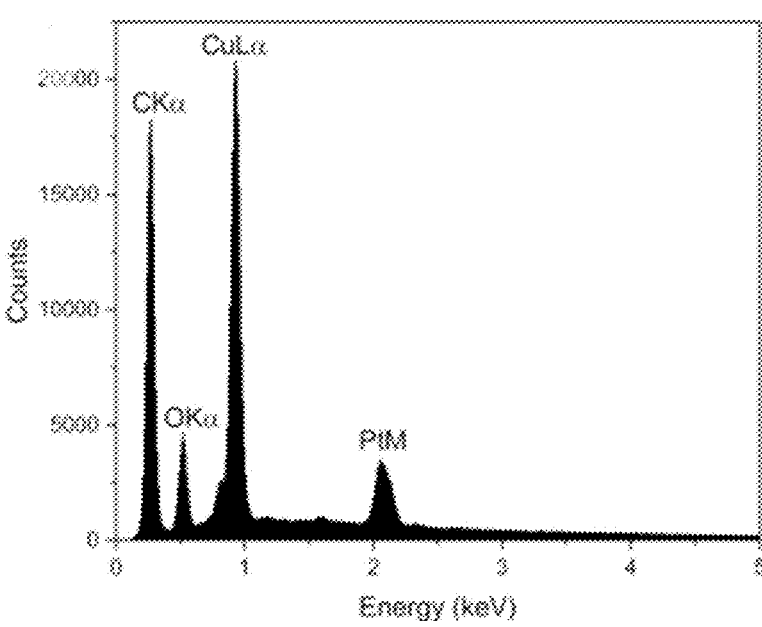

The FE-SEM image of FIG. 3A shows that the cotton fiber retained its structure despite the use of 8% NaOH in the production of the $Cu_2ONPs$, and that the cuprous oxide nanoparticles were relatively well dispersed on the fiber. As seen in FIG. 3B, further magnification revealed irregularities in the shape and size of the structures formed on the surface of the cotton fiber. The morphology and irregularities in shape and size of the $Cu_2ONPs$ present on the surface of the fibers are clearly seen in the larger magnification shown in FIG. 3C. The FE-SEM shown in FIG. 4A, and the EDS map of Cu element, where the white spots correspond to copper, shown in FIG. 4B demonstrate the uniform distribution of $Cu_2ONPs$ on the fabric surface. As seen in FIG. 4C, the EDS spectrum for a point on the surface of a treated cotton fabric confirmed the presence of Cu element with a strong peak at 0.930 keV corresponding to Cu Lα.

Figure 5A:
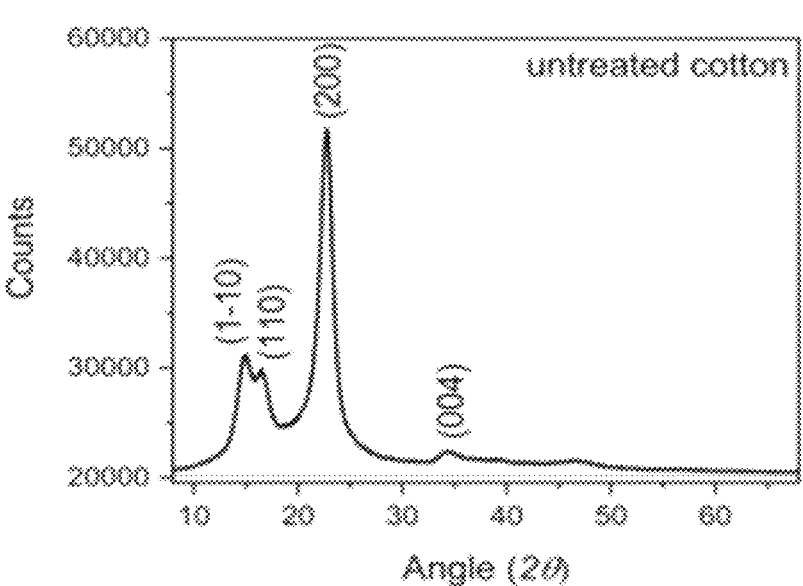
FIG. 5A and FIG. 5B depict graphs of the XRD patterns of untreated and treated fabric.
Figure 5B:
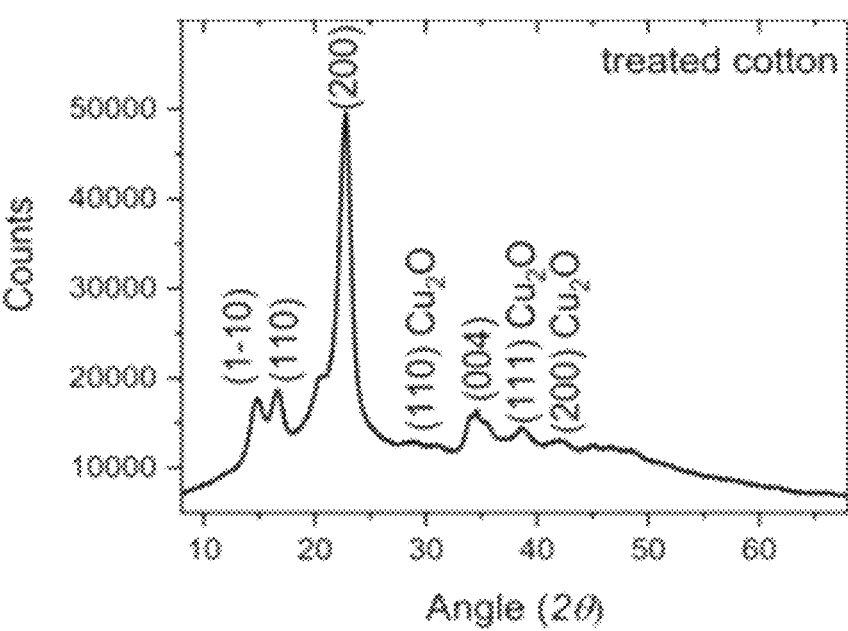

FIG. 5A and FIG. 5B present X-ray diffractograms of untreated and treated cotton. As seen in FIG. 5A, the $Cu_2ONP$-cotton fabric showed the characteristic cotton peaks at 2θ values 14.7°, 16.6°, 22.7°, and 34.8° assigned to the (1-10), (110), (200), and (004) lattice planes of cellulose Iβ, respectively. The absence of the (020) lattice plane of cellulose II indicated that the crystalline structure of cellulose was not impacted by the alkaline treatment. The presence of new peaks at 2θ values 29.7°, 36.6°, and 42.4° correspond to the (110), (111) and (200) lattice planes of $Cu_2O$, respectively, and confirm that Copper nanoparticles were successfully produced within the treated cotton fabric.

The XRD spectrum shown in FIG. 5B confirms that the treated cotton retained its crystalline structure, even in the presence of 8% NaOH.

Figure 6A:
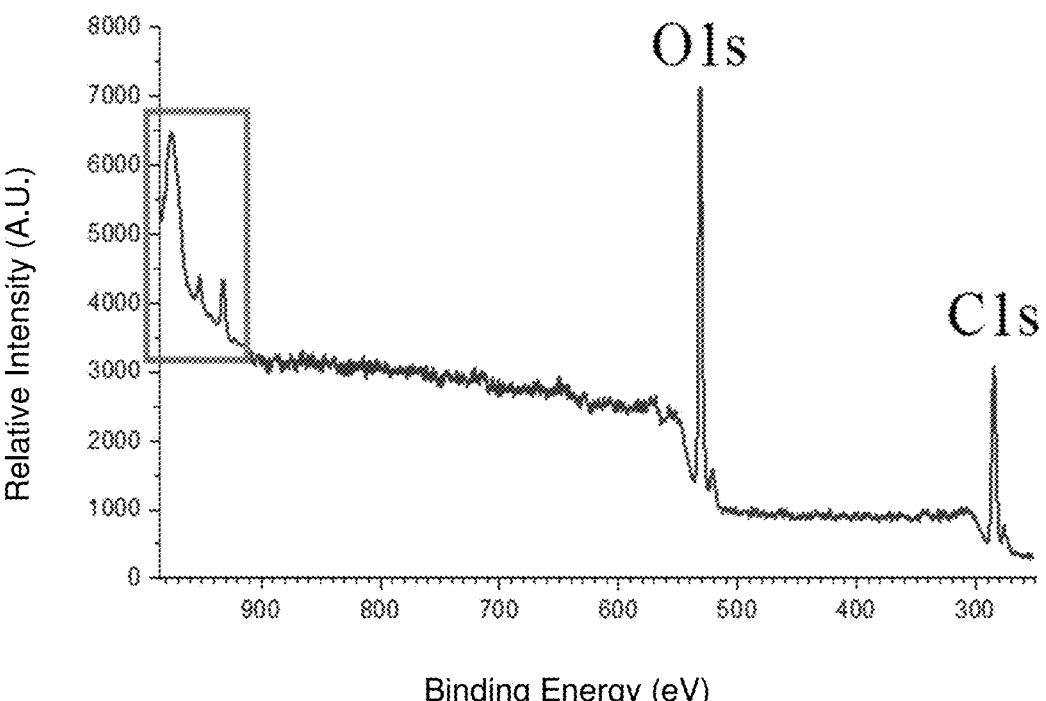
FIG. 6A and FIG. 6B depict graphs of the XPS spectrum of $Cu_2ONP$-cotton fabric.
Figure 6B:
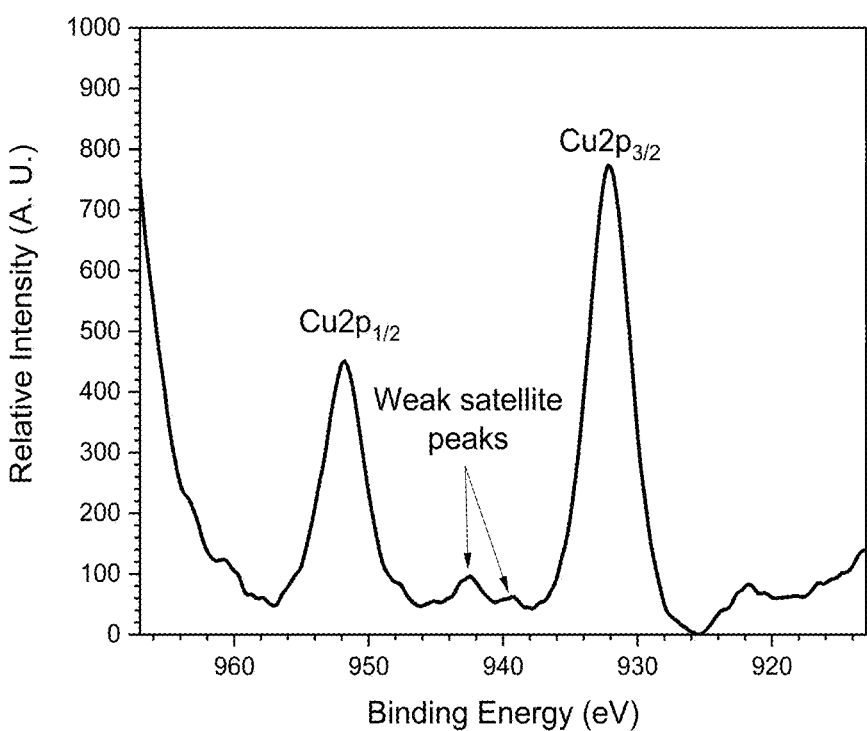

The X-ray photoelectron spectrum for the treated cotton fabric shown in FIG. 6A and FIG. 6B. As can be seen in FIG. 6A, treated cotton fabric displayed signals at 285 eV and 531 eV. These signals correspond to the C1s and O1s regions of cotton cellulose. Characteristic Cu 2p3/2 and 2p1/2 peaks for Cu (I) at 932.2 and 951.8 eV were observed in FIG. 6B, which agree with literature assignments. The weak satellite shakeup peaks for cuprous oxide ($Cu_2O$) were also present between 939 and 942 eV, confirming the reduced oxidation state of copper (I) in the nanoparticles. This data shows that the $Cu^{2+}$ ions were incorporated within the closely packed β(1-4)-linked D-glucose chain of cellulose and were thus, readily reduced to form $Cu_2O$ upon neutralization. This is conceptually similar to the Benedict's test, where copper (I) oxide is produced from the reduction of copper (II) in the presence of sugars. Prior to the instant disclosure, cellulose has only been shown to reduce copper (II) to copper (I) oxide under high pressure and high temperature conditions using an autoclave (Hage, J. L. T., et al., 1999, "Reduction of copper with cellulose in an autoclave; an alternative to electrolysis?" Miner. Eng. 12 (4):393-404. doi:10.1016/s0892-6875(99)00019-9). As depicted in FIG. 1, the stabilized $Cu^{2+}$ ions along the deprotonated alkoxide cellulose backbone were reduced under relatively mild, neutral aqueous conditions.

Figure 7A:
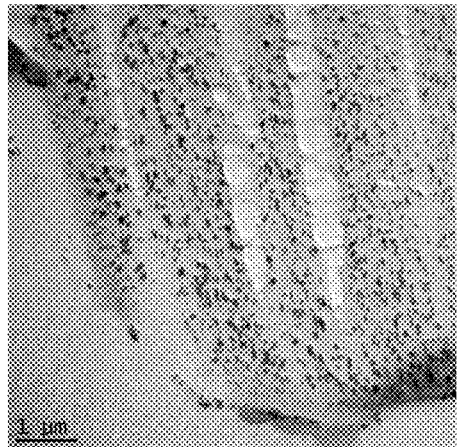
FIG. 7A to FIG. 7C depict Transmission Electron Microscopy (TEM) cross-section images of $Cu_2ONP$-cotton.
Figure 7B:
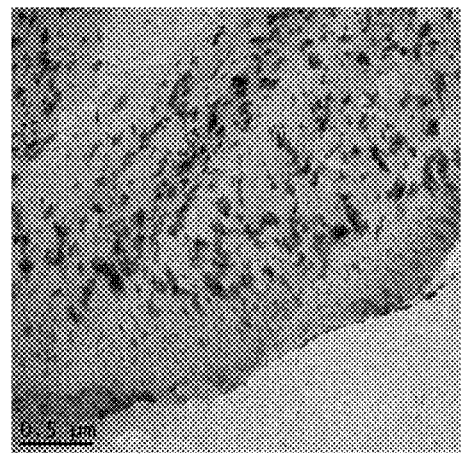
Figure 7C:
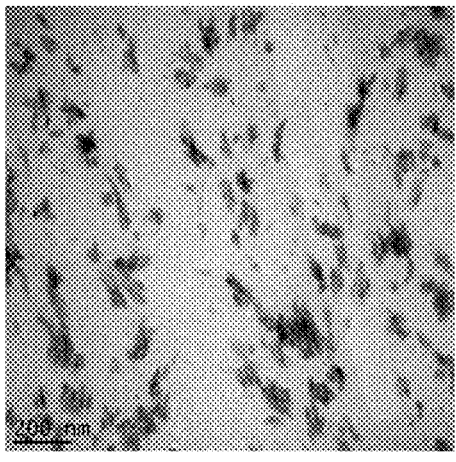

The formation of $Cu_2ONPs$ inside the cotton fiber was confirmed by using TEM to image cross-sections of treated cotton fibers. FIG. 7A presents an image of the edge and the interior of a treated cotton fiber. This image clearly shows that $Cu_2ONPs$ were fully incorporated, and uniformly dispersed throughout the entire cross-section of the fiber, without aggregates. Further magnifications of the cross-section are shown in FIG. 7B and FIG. 7C. These images show the morphology of the $Cu_2ONPs$ in the interior of the cotton fiber.

Figure 8A:
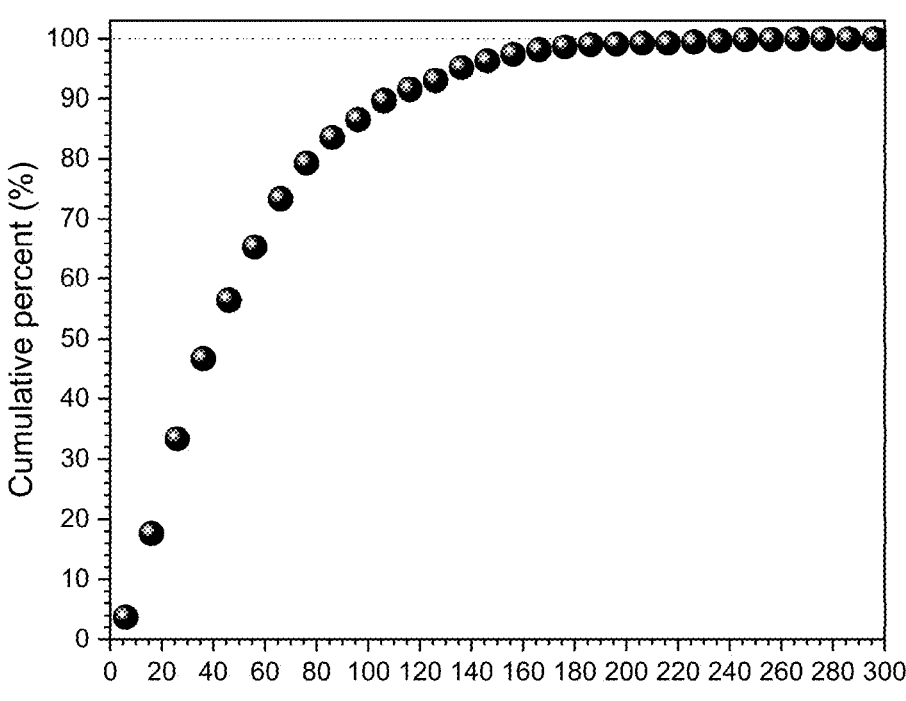
FIG. 8A and FIG. 8B depict graphs of the size distributions of cuprous oxide nanoparticles in $Cu_2ONP$-cotton fibers.
Figure 8B:
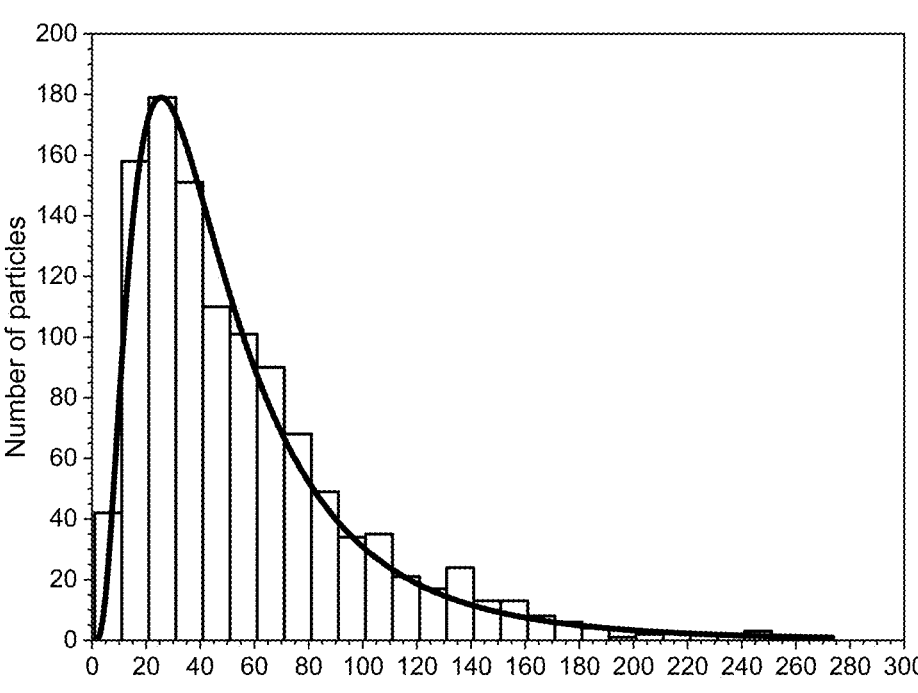

Because the nanoparticles formed were irregular in shape and size, the Feret diameter was used to calculate the average diameter of the cuprous oxide nanoparticles formed in the cellulosic fibers. The classic diameter of a shape is the distance between the two furthest points of that shape. The Feret diameter is the distance between the two furthest points of the shape measured in a given direction. As seen in FIG. 8A and FIG. 8B, the $Cu_2O$—NPs formed had a median Feret diameter of about 57.8 nm, and a maximal Feret diameter of about 72.0±51.8 nm.

In an embodiment, the internally dispersed cuprous oxide nanoparticles formed in the treated cotton fiber were evenly distributed (did not agglomerate). In an embodiment, the internally dispersed cuprous oxide nanoparticles formed in the treated cotton fiber were irregular in shape. In some embodiments of the invention, the internally dispersed cuprous oxide nanoparticles formed in the treated cotton fiber have a median Feret diameter of about 57.8 nm. In some embodiments of the invention, the internally dispersed cuprous oxide nanoparticles formed in the treated cotton fiber have a maximal Feret diameter of about 72.0±51.8 nm.

Figure 9A:
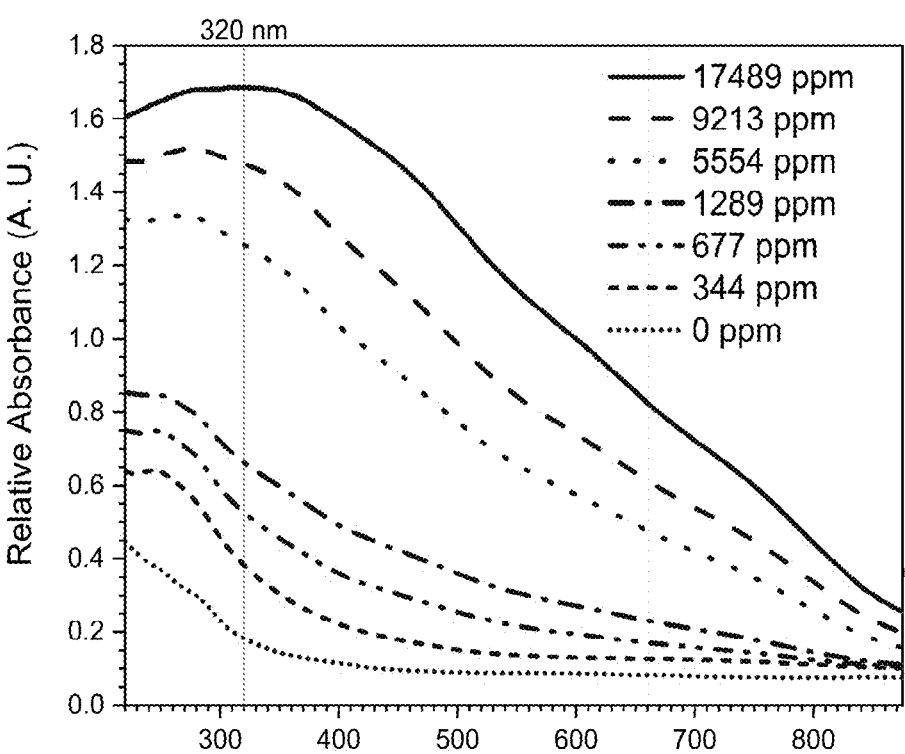
FIG. 9A and FIG. 9B depict UV-vis spectra graphs.

FIG. 9A shows the UV-vis spectra of $Cu_2ONP$-cotton with increasing concentration of copper as determined by ICP-MS by varying the concentration of $CuSO_4$ in the reaction solution. With increasing copper concentration, the UV-vis SPR intensity redshifted from a peak maximum at 242 nm for low copper concentration of about 344 ppm, to a peak wavelength of 320 nm corresponding to a significant copper content of about 17489 ppm. With increasing concentration, the proximity of the Cu$_2$ONPs formed resulted in the redshift. The observed intensity at 320 nm for each concentration was plotted as a function of increasing copper concentration is presented in FIG. 9B. The data showed a strong correlation (R2=0.9979) when fit to an exponential equation.

The literature suggests that a cuprous oxide nanoparticle concentration of about 0.1 mg/kg would have effective antiseptic properties. The concentration of internally dispersed cuprous oxide nanoparticles formed in the treated fiber varies depending on the conditions used in their formation. In an embodiment, the concentration of internally dispersed cuprous oxide nanoparticles formed in the treated fiber is at least about 000.1 mg/kg. In the examples below, the internally dispersed cuprous oxide nanoparticles formed in the treated fiber was about 17,489±15 mg/kg. In some embodiments of the invention, the concentration of internally dispersed cuprous oxide nanoparticles formed in the treated fiber may be at least about 000.1 mg/kg to about 30,000 mg/kg. In some embodiments of the invention, the concentration of internally dispersed cuprous oxide nanoparticles formed in the treated fiber may be at least about 0.001 mg/kg. In some embodiments of the invention, the concentration of Cu$_2$ONPs may be at least about 0.10 mg/kg. In some embodiments of the invention, the concentration of Cu$_2$ONPs may be at least about 0.15 mg/kg.

Cotton fibers are made into threads, yarn, and fabric in three steps: preparation, spinning, and weaving. Preparation of cotton has many steps. Cotton is first dried to reduce the moisture content, it is then cleared of debris such as dirt, seeds, burrs, stems, and leaf material. Once clean and dry, the cotton fiber is plucked from the seed by circular saws with small, sharp teeth, and packed into bales for processing. Cotton fibers are shaved from the bales and sent through a series of cleaning and drying machines. Carding machines then finish the cleaning and straightening of the fibers making them into a soft, untwisted rope called a sliver. The sliver is drawn out to a thinner strand and given a slight twist to improve strength, then wound on bobbins. The wound cotton is called roving, and the roving bobbins are ready for spinning. In the spinning process, roving is drawn and twisted into yarn and put onto bobbins. Looms then weave the cotton yarns into fabrics. Before weaving, most single spun yarns undergo the sizing (slashing) process, in which size (starch) is applied on the yarns. Sizing strengthens yarns and removes hairs (loose fibers protruding from the yarn surface) to help them withstand a wide range of mechanical stresses of bending, oscillating tension, and frictional resistance during the weaving process. Without the application of size, yarns are easily broken, causing losses in material, quality, and production time. After weaving into a fabric, the protective coating of starch is removed by a desizing process.

Cotton is currently the most widely produced natural fiber on the planet. A fabric made of 100% cotton is known for its comfort and durability. Cotton fiber can be woven or knitted into many different types of fabric, providing a slightly different feel and wear. A fabric made of 100% cotton is fully breathable, and can be cooler to wear in hot conditions. However, the breathability of a cotton fabric decreases as the thickness increases. Cotton canvas is a very durable and abrasion-resistant fabric, but it is very thick and heavy. Fabrics made of 100% cotton tend to rip and wear out easily, depending on the weave. Unless they are treated for fire-resistance, cotton fibers tend to burn away, and polyester will melt. As a natural fiber, 100% cotton garments also tend to be a bit more expensive than the synthetic counterparts. Polyester has an equal number of advantages and disadvantages as cotton. Polyester does not breathe and has a tendency to stick to the skin once perspiration begins. Polyester is a more elastic fiber than cotton, and therefore tends to be tear resistant. However, polyester does not tend to be as abrasion-resistant as cotton canvas. Polyester fabric is usually considerably cheaper than 100% cotton fabric. A fabric made from a polyester/cotton blend combines the strengths of the two fibers. Polyester/cotton garments are breathable, and tear-resistant. While not as inexpensive as pure polyester, garments made of polyester/cotton blends tend to cost less than comparable garments made of 100% cotton while providing much more comfort Cotton's strength, absorbency, and capacity to be washed and dyed make it adaptable to a considerable variety of textile products. Cotton textiles can be made into more kinds of products than textiles made with any other fiber. For example, apparel, home furnishings, and industrial products may be manufactured with cotton textiles, or textiles containing at least one cotton fiber. Textiles containing at least one cotton fiber are used in home furnishings, for example, towels, window shades, and bedding. Bedding may be bedspreads, pillowcases, pillow shams, mattress covers, and sheets. Industrial products containing textiles containing at least one cotton fiber may be wall coverings, book bindings, zipper tapes, medical supplies, industrial thread, and tarpaulins. Cotton fiber can be woven or knitted into fabrics such as velvet, corduroy, chambray, velour, jersey, and flannel. Additionally, textiles containing at least one cotton fiber may be used for apparel products such as underwear, socks, and t-shirts. Textiles containing at least one cotton fiber may also be used in the preparation of fishnets, coffee filters, book binding, and archival paper. Textiles containing at least one cotton fiber may also be used to produce goods such as bandages, swabs, bank notes, or cotton swabs or buds.

Figure 9B:
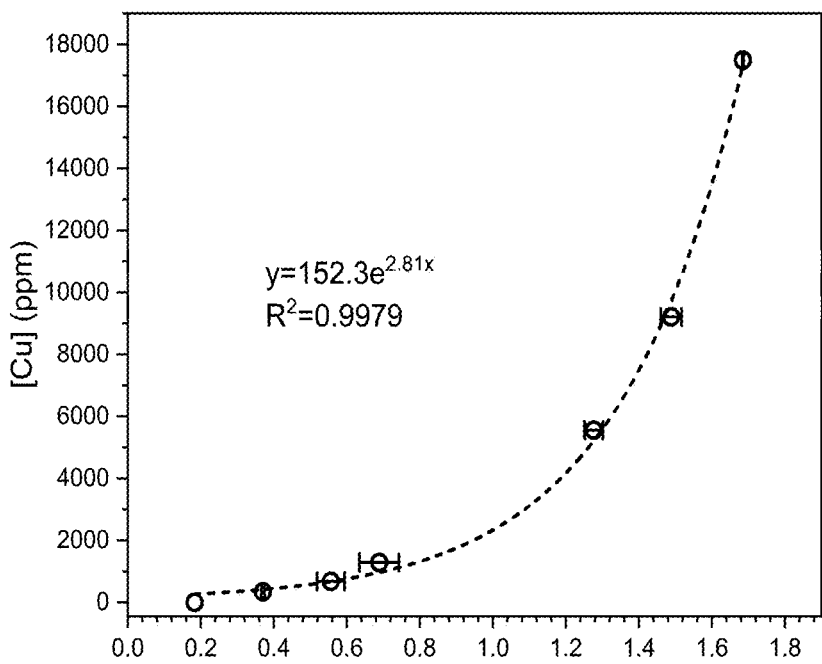

The washing durability and copper-release behavior of the treated fabrics were investigated using a simulated accelerated home laundering procedure, and the copper content was determined by inductively coupled plasma-mass spectrometry (ICP-MS) and UV-vis spectroscopy. The Cu$_2$ONP-cotton fabrics were laundered according to the AATCC test method 61-2007. Copper concentrations were determined using ICP-MS by acid digestion of laundered Cu$_2$ONP-cotton fabrics, and using the calibration curve shown in FIG. 9B, for treated fibers laundered for 0, 5, 10, 20, 30, 40, or 50 cycles. As seen in FIG. 9A and FIG. 9B, as the number of laundering cycles increased, there was a slight decrease in absorbance at 320 nm. After five launderings the amount of copper released from Cu$_2$ONP-cotton fabric was only about 9%, and after 50 cycles the fabric had only lost about 19% of the copper nanoparticles. There was strong agreement between the values determined by the UV-vis calibration curve and by ICP-MS, which determines overall copper content irrespective of speciation. The initial drop in copper can be attributed to Cu$_2$ONPs on the exterior of the cotton fiber; since the surface-bound Cu$_2$ONPs were adsorbed electrostatically, it may be that these nanoparticles could be detached from the fiber surface through mechanical agitation during the laundering process. The copper release behavior exhibited a leveling effect upon additional laundering cycles. Not wishing to be bound by theory, it is believed that this drop was the result of the removal of most of the surface-bound nanoparticles from the surface of the treated cotton fiber during the first few laundering cycles.

Figure 10:
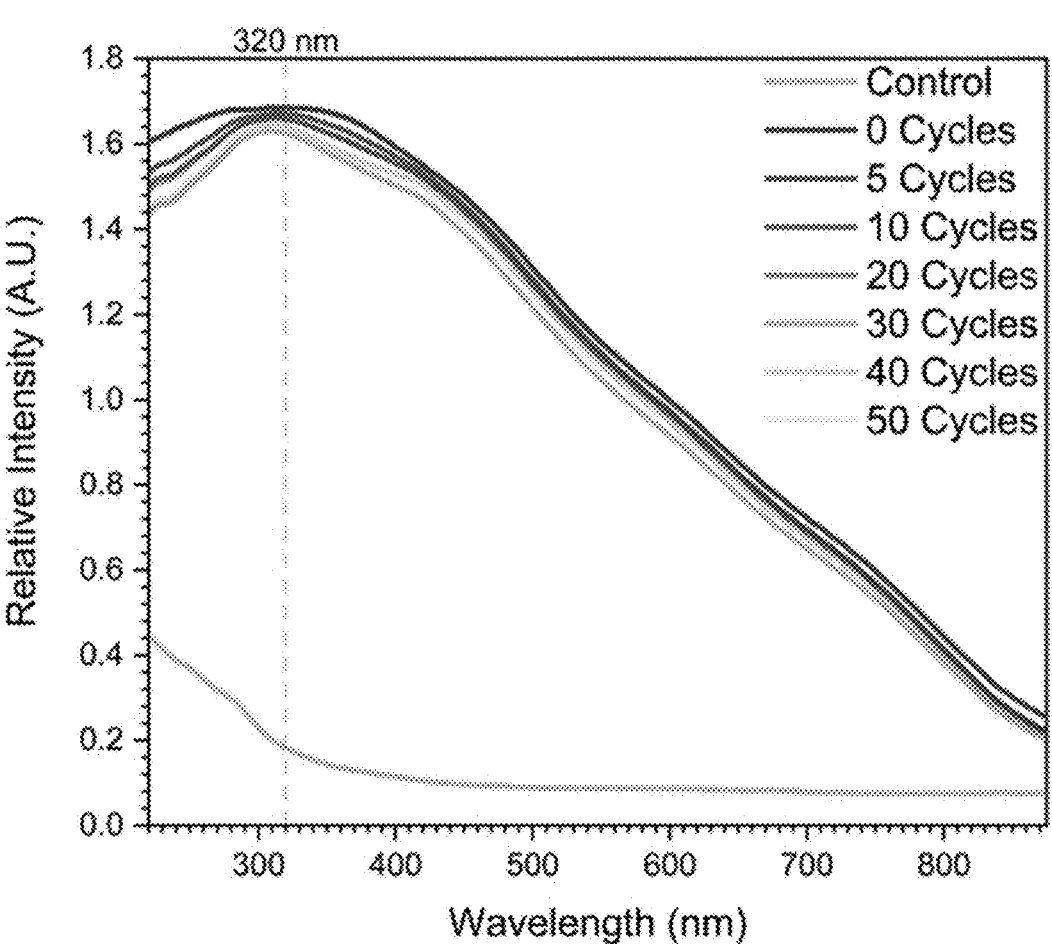
FIG. 10 depicts a graph of the UV-vis absorbance spectra obtained from control and $Cu_2ONP$-cotton fabrics after incremental home launderings in a detergent solution. Y axis shows the relative absorbance intensity in absorbance units (A.U); X axis shows the wavelength in nm.

As shown in FIG. 10, examination of the $\lambda_{max}$ across sequential launderings revealed a blueshift in the peak wavelength from 320 nm at 0 cycles to a lower wavelength of 310 nm after at least 5 cycles. This blueshift in wavelength may be attributed to small changes in the surface chemistry of the Cu$_2$ONPs during the laundering since there is not a significant difference in copper concentration released after 30 to 50 laundering cycles. It is possible that the surfactants and salts present in the detergent can partially oxidize the nanoparticle surface from copper (I) to copper (II), consistent with literature values of CuO $\lambda_{max}$ between 270 nm and 310 nm.

In an embodiment, the invention relates to treated cellulosic fibers comprising internally dispersed cuprous oxide nanoparticles, where at least about 20% of the cuprous oxide nanoparticles remain in the treated fiber after at least about 5 laundering cycles. In some embodiments of the invention, at least about 40% of cuprous oxide nanoparticles remain in the cellulosic fiber comprising internally dispersed cuprous oxide nanoparticles after at least about 5, 10, 15, 20, 25, 30, 35, 40, 45, or 50 laundering cycles. In some embodiments of the invention, after at least 5, 10, 15, 20, 25, 30, 35, 40, 45, or 50 laundering cycles the cellulosic fiber comprising internally dispersed cuprous oxide nanoparticles retains at least about 40%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99% of the copper oxide nanoparticles as measured by ICP-MS. In some embodiments of the invention, after at least 5, 10, 15, 20, 25, 30, 35, 40, 45, or 50 laundering cycles cellulosic fiber comprising internally dispersed cuprous oxide nanoparticles retains at least about 40%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99% of the cuprous oxide nanoparticles as measured by surface plasmon resonance absorption peak intensity.

In an embodiment, the invention relates to a method for preparing a treated cellulosic fiber comprising internally dispersed cuprous oxide nanoparticles. The method comprises immersing a cellulosic fiber in a solution comprising a copper (II) precursor and a base to produce a copper complex [Cu(OH)$_4$]$^{2-}$ that diffuses through the interior of the cellulosic fiber; transferring the cellulosic fiber with the diffused [Cu(OH)$_4$]$^2$ copper complex to water to produce a Cu(OH)$_2$ complex in the fiber; and allowing the cellulosic fiber comprising the Cu(OH)$_2$ complex to dry, to prepare a treated cellulosic fiber comprising internally dispersed cuprous oxide nanoparticles. In some embodiments of the invention, the water to which the cellulosic fiber with the diffused [Cu(OH)$_4$]$^{2-}$ copper complex is transferred may be tap water, spring water, or purified water. The water to which the cellulosic fiber with the diffused [Cu(OH)$_4$]$^{2-}$ copper complex is transferred may be water purified by any method known in the art, such as by deionization, reverse osmosis, or distilling. Immersion of the cellulosic fiber with the diffused [Cu(OH)$_4$]$^{2-}$ copper complex in water causes the formation of cellulosic fiber comprising the Cu(OH)$_2$ complex. In some embodiments of the invention, the water to which the cellulosic fiber with the diffused [Cu(OH)$_4$]$^{2-}$ copper complex is transferred is heated. The water to which the cellulosic fiber with the diffused [Cu(OH)$_4$]$^{2-}$ copper complex is transferred may be at about room temperature (about 23° C.), or may be heated to at least 30° C., at least 40° C., at least 50° C., at least 60° C., at least 70° C., at least 80° C., at least 90° C., at least 100° C., or a portion thereof.

Using the methods of the invention, the resulting cellulosic fibers comprising internally dispersed cuprous oxide nanoparticles are produced without effecting the internal crystalline structure of the fibers.

Cotton fabrics with multifunctional properties infused with metal oxide nanoparticles for antibacterial applications are becoming increasingly popular. Copper oxide nanomaterials have gained popularity for their synthetic versatility, microbicidal properties, and cost-effectiveness compared to nanomaterials from other metals. One limitation to these antimicrobial agents when applied to commercial textiles is reduced efficacy after continuous use and laundering cycles. After 50 laundering cycles, Cu$_2$ONP-cotton fabric was further studied for its antibacterial and antifungal properties. The AATCC test method 100-2007 was used with the gram-positive *Staphylococcus aureus*. After just 24 hours, the Cu$_2$ONP-cotton fabric exhibited 99.995% inhibition against gram-positive bacteria *Staphylococcus aureus*, with 10$^6$ fewer colony forming units compared to control cotton at time zero. The treated fibers of the invention retained greater antibacterial properties when compared to cotton fabrics with externally applied Cu$_2$O nanoparticles (Sharma P., et al., 2019, "Green synthesis and characterization of copper nanoparticles by *Tinospora cardifolia* to produce nature-friendly copper nano-coated fabric and their antimicrobial evaluation," J. Microbiol. Methods 160:107-116; doi:10.1016/j.mimet.2019.03.007), and thiol-treated cotton with internally formed copper nanoparticles (Gouda M., et al., 2015, "Preparation and Characterization of Some Nanometal Oxides Using Microwave Technique and Their Application to Cotton Fabrics," J. Nanomater. 2015:1-9. doi: 10.1155/2015/586904). After 50 laundering cycles the externally applied copper nanoparticles exhibited only about 65% bacterial inhibition, and the thiol-conjugated nanoparticles exhibited less than about 99% after just 10 laundering cycles in non-ionic detergent.

The antifungal activity of the Cu$_2$ONP-cotton fabric was also tested using AATCC test method 30 Test III using fungus *Aspergillus niger*. After 50 laundering cycles the Cu$_2$ONP-cotton fabric inhibited all fungal growth after 7 days, even in a growth promoting environment. The *Aspergillus niger* spore colonies did not grow on the cuprous oxide nanoparticle fabric but grew on the control fabric. FIG. 12A and FIG. 12B depict graphs of the bacteria and fungi reduction by Cu$_2$ONP-cotton fabric after 50 laundering cycles. These figures show that, even after 50 laundering cycles, Cu$_2$ONP-cotton fabric of the invention was able to reduce about 100% of *S. aureus* and *A. niger*. These results show that treated cellulosic fibers comprising internally dispersed cuprous oxide nanoparticles are useful in antimicrobial, anti-fungal, or anti-viral yarns, threads, twines, ropes, cloth, woven fabrics, knitted fabrics, film-based composites, nonwoven fabrics, or final articles. The treated cellulosic fibers comprising internally dispersed cuprous oxide nanoparticles are useful in antimicrobial, anti-fungal, or anti-viral final articles that comprise all or part of athletic wear, an undergarment, military wear, a medical textile, or a functional barrier. In some embodiments of the invention the final article comprising at least one treated cellulosic fiber comprising internally dispersed cuprous oxide nanoparticles is all or part of an antimicrobial, anti-fungal, or anti-viral packaging. In some embodiments of the invention, the final article comprising at least one treated cellulosic fiber comprising internally dispersed cuprous oxide nanoparticles is an antimicrobial, anti-fungal, or anti-viral agricultural or food packaging.

In an embodiment, the invention relates to an article comprising at least one treated cellulosic fiber comprising internally dispersed cuprous oxide nanoparticles; where the cellulosic fiber maintains its internal structure.

In an embodiment, the invention relates to an article comprising at least one cellulosic fiber comprising internally dispersed cuprous oxide nanoparticles. In some embodiments of the invention, the article comprising at least one cellulosic fiber comprising internally dispersed cuprous oxide nanoparticles is a yarn, a thread, a twine, a rope, a cloth, a woven fabric, a knitted fabric, a film-based composite, a nonwoven fabric, or all or part of a final article. In some embodiments of the invention, the final article comprising at least one cellulosic fiber comprising internally dispersed cuprous oxide nanoparticles is athletic wear, an undergarment, military wear, a medical textile, or a functional barrier. In some embodiments of the invention, the final article comprising at least one cellulosic fiber comprising internally dispersed cuprous oxide nanoparticles is a surgical gown, an isolation gown, a lab coat, a glove, surgical scrubs, a head cover, a hair cover, a face mask, a floor mat, a lamp handle cover, an exam table cover, a cast liner, a splint liner, a mattress cover, a sheet, a comforter cover, a pillow case, a pillow cover, a towel, clothing, underwear, a sock, shoe-cover, a protective garment for military or other use, apparel for food handling. In some embodiments of the invention, the final article comprising at least one cellulosic fiber comprising internally dispersed cuprous oxide nanoparticles is athletic wear, an undergarment, military wear, a medical textile, a washable or disposable sanitizing wipe, a functional barrier, a towel, a bedding, a shoe liner, a garment liner, or a curtain. In some embodiments of the invention, the medical textile comprising at least one cellulosic fiber comprising internally dispersed cuprous oxide nanoparticles is a curtain, a bedding, a surgical arena fabric, a surgical personnel protective garment, a wound or non-wound patient dressing, a bandage, a gauze, a packing, or a cleaning material.

In an embodiment, the cellulosic fibers comprising internally dispersed cuprous oxide nanoparticles may be used for the manufacture of antimicrobial packaging. Antimicrobial packaging may be used to enhance safety in food, healthcare, and personal-care markets. In some embodiments of the invention, the antimicrobial packaging may be used for shipping agricultural products, or for the preservation of processed food materials. Packaging prepared with at least one cellulosic fiber comprising internally dispersed cuprous oxide nanoparticles may be used for the transportation and storage of meats. For example, for the packaging of beef, fish, pork, poultry, etc. A cellulosic fiber comprising internally dispersed cuprous oxide nanoparticles may also be used in barriers and/or films to separate the food material and/or packaging from liquids such as water or moisture.

In an embodiment of the invention, at least one treated cellulosic fiber comprising internally dispersed cuprous oxide nanoparticles of the invention is blended with at least one other type of fiber. In some embodiments, at least one other type of fiber is an animal-based fiber, a plant-based fiber, a mineral-based fiber, and a synthetic fiber. Animal-based fibers include at least alpaca, angora wool, byssus, camel hair, cashmere wool, chiengora, lambswool, llama, mohair wool, qiviut, rabbit, silk, vicuna, and sheep wool. Plant-based fibers include at least abaca, wood pulp (acetate), bamboo, banana, kapok, coir (coconut), flax, hemp, jute, kenaf, lyocell, modal, raffia, raw ramie, rayon, and sisal. Synthetic fibers include at least acrylic, Kevlar, modacrylic, nomex, nylon, polyester, polypropylene, spandex, and rayon. The resulting fiber will retain the functional attributes of the treated cellulosic fiber comprising internally dispersed cuprous oxide nanoparticles of the invention.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

As used herein, the term "about" is defined as plus or minus ten percent of a recited value. For example, about 1.0 g means 0.9 g to 1.1 g.

As used herein, the term "dispersed" is defined as distributed evenly. As used herein, the term "distributed evenly" refers to cuprous oxide nanoparticles equally spread throughout a treated cellulosic fiber.

As used herein, a "Feret diameter" refers to the longest distance possible measurable on a cuprous oxide nanoparticle.

As used herein, the terms "Cu$_2$ONPs" and "cuprous oxide nanoparticles" are used interchangeably and refer to the cuprous oxide structures formed on the surface and internally dispersed in cotton fabrics when using the methods of the invention.

In the instant application, "Cu$_2$ONP-cotton fabric" refers to cotton fabric containing dispersed cuprous oxide nanoparticles of the invention.

Embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby. All publications, patents, and patent applications mentioned in this specification are herein incorporated by reference to the same extent as if each individual publication, patent, or patent application was specifically and individually indicated to be incorporated by reference.

EXAMPLES

Having now generally described this invention, the same will be better understood by reference to certain specific examples, which are included herein only to further illustrate the invention and are not intended to limit the scope of the invention as defined by the claims.

Example 1

Formation of Copper Oxide Nanoparticles in Cotton Fibers

Copper oxide nanoparticles were formed in bleached and desized cotton fabrics.

Bleached and desized cotton print cloth fabric was purchased from Testfabrics, Inc. (West Pittston, Pennsylvania, USA). Copper sulfate anhydrous (CuSO$_4$, ≥99.99%), and sodium hydroxide solution (NaOH, 50% w/v) were purchased from Sigma-Aldrich (St. Louis, Missouri, USA). All chemicals were used without further purification.

To 80 mL of water was dissolved 0.250 g copper sulfate anhydrous. To the stirring solution of copper sulfate was slowly added 20 mL of 50% w/v sodium hydroxide solution. Upon addition of sodium hydroxide the clear light blue solution ($CuSO_4$) initially precipitated a light blue solid ($Cu(OH)_2$), which dissolved upon complete addition of the 20 mL of 50% w/v sodium hydroxide solution to become a clear dark blue solution ($[Cu(OH)_4]^{2-}$). A 50 mm×200 mm swatch of bleached and desized cotton print cloth fabric was added to a 50 mL centrifuge tube and 40 mL of $[Cu(OH)_4]^{2-}$ solution was added. The centrifuge tube was mixed at 750 rpm for 30 minutes using an Advanced Vortex Mixer (Fisher Scientific; Hampton, New Hampshire, USA). The fabric changed from a white to dark blue color. The fabric was then removed from the solution, and rinsed with Deionized (DI) water to remove excess copper precursor and sodium hydroxide. The fabric changed from dark blue to light blue when the excess base had been neutralized. The fabric was added to 80° C., where the light blue fabric changed immediately to dark brown. The fabric was removed, rinsed in DI water, and air dried at room temperature.

A reaction schematic for the formation of copper oxide nanoparticles in cotton is shown in FIG. 1. This figure shows that when sodium hydroxide was added to the copper sulfate soaking solution, the hydroxides coordinated to the $Cu^{2+}$ metal center and precipitated the insoluble $Cu(OH)_2$ complex. Upon further addition of sodium hydroxide, the insoluble $Cu(OH)_2$ was solubilized by the formation of $[Cu(OH)_4]^{2-}$. When a cotton fabric was immersed in a bath of dissolved copper sulfate, the light blue color of the fabric was readily rinsed away. Alternatively, the excess hydroxide present in the highly alkaline $[Cu(OH)_4]^{2-}$ deprotonated the hydroxides of the cellulose backbone. This was necessary for the incorporation of copper to the internal structure of the cotton fiber. The 4-coordinate copper center strongly associated with the closely-packed alkoxides of the deprotonated cellulose chains. The dark blue color of the $[Cu(OH)_4]^{2-}$ cotton fabric remained when the cotton fabric was rinsed with alkaline water. As the cotton fabric was rinsed with neutral water, the treated cotton fabric changed from dark blue to light blue. This color change correlated with the transition from a $[Cu(OH)_4]^{2-}$ to $Cu(OH)_2$, and did not wash off from the fabric as the water-insoluble copper complex diffused through the interior of the microfibrillar structure of the cotton. Subsequent immersion of the fabric in 80° C. DI water resulted in the fabric turning brown due to the production of internally dispersed copper oxide nanoparticles ($Cu_2ONPs$).

This example describes the method used to prepare treated cellulosic fibers comprising internally dispersed cuprous oxide nanoparticles.

Example 2

Characterization of Internally Dispersed Copper

The copper nanoparticles formed were analyzed to determine their distribution inside and outside of the cotton fibers.

To observe the internal dispersion of $Cu_2ONPs$ within the cotton fiber, a procedure developed at the Southern Regional Research Center was used (Boylston, E. et al., 1991, "*A quick embedding method for light and electron microscopy of textile fibers*," Biotech. Histochem. 66 (3): 122-124; and Thibodeaux, D. P. and Evans, J. P., 1986, "*Cotton fiber maturity by image analysis*," Text. Res. J. 56: 130-139). Briefly, fibers from the treated cotton fabric were combed and immersed in a methacrylate matrix solution (mixture of methyl metacrylate and butyl methacrylate) in TEFLON fluorinated hydrocarbon polymer tubing (3.2 mm inner diameter), which was polymerized using UV light for 30 minutes. The resulting block of encased fiber was removed from the TEFLON fluorinated hydrocarbon polymer tubing and immobilized in BEEM embedding capsules. Using a PowerTome Ultramicrotome (Boeckeler Instruments, Inc.; Tucson, Arizona, USA), the fibers were sliced into sections of about 100-120 nm to be examined using Transmission Electron Microscopy (TEM). For TEM analysis, the sections were placed on a carbon-film-coated copper grid. The polymer matrix was then dissolved using methyl ethyl ketone.

To image $Cu_2ONPs$ prepared inside cotton fibers, a TEM (FEI Tecnai G2 F30) operating at 300 kV was used. Field emission scanning electron microscopy (FE-SEM) equipped with energy-dispersive X-ray (EDS) spectroscopy was used to examine external morphology and surface composition of $Cu_2ONP$-cotton fibers using an SEM (JSM-6610 LV, JEOL) operating with an acceleration voltage of 5.0 keV. Samples for FE-SEM analysis were prepared with a carbon coating. Copper oxide particle sizes were measured using TEM images by counting particles with IMAGEJ software (National Institutes of Health). Size and distribution of the particles were determined from a representative sample of 924 particles.

Untreated fabrics were tan in color, the air-dried $Cu(OH)_2$-incorporated fabric, and the oven-dried $Cu(OH)_2$-incorporated fabric appeared light green, and the fabric containing the $Cu_2ONP$ appeared brown. The UV-vis spectra of the untreated and the treated cotton fabrics are shown in FIG. 2. This figure shows that incorporation of $Cu(OH)_2$ into the fabric gave an increase in the absorbance at 290 nm with a second peak at 713 nm; this corresponds to a transition from the untreated fabric to the air-dried ($Cu(OH)_2$) fabric. The $Cu(OH)_2$ was very stable when the fabric was dried; little change was observed in the absorbance spectrum and the color when the fabric was heated in an oven to 150° C. for several hours ($Cu(OH)_2$). The UV-vis spectrum and color of the fabric remained essentially unchanged. Alternatively, as the neutralized-treated cotton fabric was immersed in an 80° C. water bath, the fabric color changed immediately to a dark brown color. The UV-vis spectrum for the brown cotton fabric showed a peak at 320 nm, which corresponds to the surface plasmon resonance of the newly formed copper oxide. The important role water plays in the hydrothermal production of copper oxide is demonstrated by the formation of copper oxide only in aqueous solution—not in air, or in the dried fabric.

X-ray diffractograms (XRD) of the cotton fabric fibers were collected using a PANalytical Empyrean X-ray Diffractometer (Malvern Panalytical, Malvern, UK) with Cu Kα radiation (1.54060 Å) and generator settings of 45 kV and 40 mA. Angular scanning was collected from 5.0 to 80° 2θ with a step size of 0.0260° and rate of 0.6°/min. X-ray photoelectron spectroscopy (XPS) measurements were collected using a VG Scientific ESCALAB MKII (Thermo Scientific, Waltham, Massachusetts, USA) spectrometer system using an A1Kα as an excitation source (hv=1486.6 eV). The chamber pressure during analysis was <2×10-8 mbar. Generally, data acquisition was collected with dwell times of 6 seconds per data point. To improve signal-to-noise at regions of interest the dwell time per data point was increased to 60 seconds per point for C1s and O1s, and 200 seconds per point for $Cu_2p$. After data acquisition the signal of each data point was rescaled to dwell times of 60 seconds. The spectrum was calibrated by reference to the C1s peak at 284.8 eV binding energy.

The FE-SEM images and EDS mapping were used for determining the size, morphology and composition of the particles formed on the cotton fibers collected from isolated microfibrils. As shown in FIG. 3A, despite using an 8% sodium hydroxide solution to produce $Cu_2ONP$-cotton the fiber retained its original shape. This was further confirmed based on the XRD spectrum shown in FIG. 4B. The absence of the (020) lattice plane of cellulose II agrees that the crystalline structure of cellulose was not impacted by alkaline treatment. As seen in FIG. 3B, further magnification of the cotton fiber revealed the formed irregularly-shaped cuprous oxide nanoparticles ($Cu_2ONPs$). The morphology of the nanoparticles are notable for their high surface-area-to-volume due to irregularity in shape and size. As seen on FIG. 3C, large aggregates of $Cu_2ONPs$ were present on the surface of the fibers. The FE-SEM shown in FIG. 4A, and the EDS map of Cu element shown in FIG. 4B, where the white represents copper, demonstrated the uniform distribution of $Cu_2ONPs$ on the fabric surface. The EDS spectrum for a point on the surface of the cotton fabric is shown in FIG. 4C, and confirms the presence of Cu element with a strong peak at 0.930 keV corresponding to CuLα.

The X-ray diffractograms of the $Cu_2ONP$-cotton fabric of FIG. 5A and FIG. 5B show the characteristic cotton peaks at 2θ values 14.7°, 16.6°, 22.7°, and 34.8° assigned to the (1-10), (110), (200), and (004) lattice planes of cellulose Iβ, respectively. Note the absence of the (020) lattice plane of cellulose II in FIG. 5B, which further indicates that the crystalline structure of cellulose was not impacted by the alkaline treatment. The presence in FIG. 5B of new peaks at 2θ values 29.7°, 36.6°, and 42.4° correspond to the (110), (111) and (200) lattice planes of $Cu_2O$, respectively, and confirm that the Cu nanomaterials were successfully produced and immobilized within the cotton fabric.

The X-ray photoelectron spectrum for the $Cu_2O$-cotton fabric is shown in FIG. 6A and FIG. 6B. As seen at FIG. 6A, the $Cu_2O$-cotton fabric displayed signals at 285 eV and 531 eV corresponding to the C1s and O1s regions, respectively of cotton cellulose. Additionally, characteristic Cu $2p_{3/2}$ and $2p_{1/2}$ peaks for Cu (I) at 932.2 and 951.8 eV were observed, which agree with the literature assignments. The weak satellite shakeup peaks for cuprous oxide ($Cu_2O$) were also present between 939 eV and 942 eV, confirming the reduced oxidation state of copper (I) in the nanoparticles, whereas copper (II) oxide (CuO) would have strong, well resolved peaks in nearly the same intensity as the Cu 2p3/2 signals. The data show that the $Cu^{2+}$ ions are incorporated within the closely packed β(1-4) linked D-glucose chain of cellulose, and are, thus, readily reduced, and form $Cu_2O$ upon neutralization. This is conceptually similar to the Benedict's test, where copper (I) oxide is produced from the reduction of copper (II) in the presence of sugars. Previously, cellulose has only been shown to reduce copper (II) to copper (I) oxide under high pressure and temperature conditions using an autoclave (Hage J L T, et al., 1999 "Reduction of copper with cellulose in an autoclave; an alternative to electrolysis?," Miner. Eng. 12 (4): 393-404. doi:10.1016/s0892-6875 (99)00019-9). In the instant example, the stabilized $Cu^{2+}$ ions along the deprotonated alkoxide cellulose backbone were reduced under relatively mild, neutral aqueous conditions.

The formation of $Cu_2ONPs$ inside the cotton fibers was confirmed by imaging the copper-fiber nanocomposite cross-section by TEM. $Cu_2ONPs$ were observed within the interior of the cotton fiber. FIG. 7A presents an image of the edge and interior of the cotton fiber which clearly shows the full incorporation of $Cu_2ONPs$ within the fiber. Further magnification of the cross-section in FIG. 7B and FIG. 7C show the morphology of the $Cu_2ONPs$ in the interior of the cotton fiber are irregular in shape and size. Because these nanocomposites are irregular in shape and size, the Feret diameter—the longest distance possible in any direction—was used to calculate the average diameter. As seen in FIG. 8A and FIG. 8B, the median and mean sizes for the maximal Feret diameter were 57.8 nm and 72.0±51.8 nm, respectively.

The concentrations of copper in the fabric were determined using inductively coupled plasma mass spectrometry (ICP-MS) at the University of Utah ICP-MS Metals Laboratory (Salt Lake City, Utah, USA). Briefly, 0.500 g of treated fabric was placed in a microwave reactor vessel containing 9.5 mL of 34% nitric acid solution. The reactor vessel was irradiated with microwaves using a Mars 6 230/60 microwave reactor (CEM Corporation; Matthews, North Carolina, USA) for 60 minutes. The digest was diluted 1:10 w/w with a final internal standard concentration of 10 ppb indium. Concentrations were determined using an external calibration curve using copper single element standard (Inorganic Ventures; Christiansburg, Virginia, USA).

UV-vis absorbance spectra were collected for the wavelength range of 220 to 800 nm with a step size of 1.0 nm using a UV/Vis/NIR spectrophotometer (ISR-2600; Shimadzu; Columbia, Maryland, USA). Spectral data were analyzed using Origin 2018b Graphing & Analysis software from OriginLab (Northampton, Massachusetts, USA).

FIG. 9A shows the UV-vis spectra of $Cu_2ONP$-cotton with increasing concentration of Cu as determined by ICP-MS by varying the concentration of $CuSO_4$ in the reaction solution. With increasing Cu concentration, the UV-vis SPR intensity redshifted from a peak maximum at 242 nm for low concentration (344 ppm) to a peak wavelength of 320 nm corresponding to a significant 17489 ppm Cu content. With increasing concentration there was greater aggregation of $Cu_2ONPs$ resulting in redshift. The observed intensity at 320 nm for each concentration was plotted as a function of increasing copper concentration and is presented in FIG. 9B. The data showed a strong correlation ($R2=0.9979$) when fit to an exponential equation. This method was further applied to determine the concentrations of Cu present in laundered fabrics and compared with concentrations determined directly by ICP-MS.

This example describes the characteristics of the cuprous oxide nanoparticles formed internally dispersed in cellulosic fabric.

Example 3

Laundering Durability of Internally Dispersed Cuprous Oxide Nanoparticles

To determine the wash stability of the internally dispersed cuprous oxide nanoparticles formed by the method taught herein, fabrics comprising internally dispersed cuprous oxide nanoparticles were subjected to laundering cycles, and the amounts of copper determined.

Washing of copper oxide-treated cotton was conducted following the AATCC Test Method 61-2007: Colorfastness to Laundering: Accelerated, using a laboratory washing machine, Launder-Ometer (M228-AA, SDL Atlas, LLC). A stainless steel canister containing 200 mL of 0.37 w/v ionic detergent solution in DI water (TIDE; Procter & Gamble Co.; Cincinnati, Ohio, USA) and ten stainless steel balls (6.35 mm diameter) was preheated to 40±0.1° C. in the laboratory washing machine. A treated fabric swatch (50 mm×200 mm) was added to the preheated canister and rotated at the constant temperature of 40±0.1° C. and constant rate of 40±2 rpm for 45 minutes. One laundering cycle using the stainless steel balls and washing conditions for the accelerated laundering procedure is equivalent to five at-home or commercial laundering cycles. The fabric swatches were washed consecutively up to a maximum of 50 cycles. After the desired number of simulated laundering cycles were completed, the canister was removed from the washing machine, the fabric swatch was rinsed in room temperature DI water for 5 minutes, and air-dried at room temperature. The percent copper remaining was determined by ICP-MS from acid digestion of Cu$_2$ONP-cotton fabrics, and by UV-vis calibration curve and presented as percent copper remaining:

$$[Cu](\%) = \frac{l_0 - l_n}{l_0} \times 100 \qquad (1)$$

where $l_0$ and $l_n$ are the concentrations of copper determined by ICP-MS or UV-vis for 0 cycles and $n^{th}$ cycles, respectively.

The Cu$_2$ONP-cotton fabrics were laundered according to the AATCC test method 61-2007. Copper concentrations were determined by ICP-MS by acid digestion of laundered Cu$_2$ONP-cotton fabrics, and by the calibration curve determined above, for the treated cellulosic fibers before laundering, and after 5, 10, 20, 30, 40, and 50 laundering cycles. The percent copper remaining in the Cu$_2$ONP-cotton fabric after each laundering cycle was calculated using Equation 1. As the number of laundering cycles increased, there was a slight decrease in absorbance at 320 nm. After five launderings the amount of copper released from Cu$_2$ONP-cotton fabric was only 9%, and after 50 cycles the fabric only lost 19%. There was strong agreement between the values determined by the previously determined UV-vis calibration curve and ICP-MS, which determines overall copper content irrespective of speciation. The initial drop in copper can be attributed to Cu$_2$ONPs on the exterior of the cotton fiber; since the surface-bound Cu$_2$ONPs were adsorbed electrostatically, the nanoparticles could be detached from the fiber surface through mechanical agitation during the laundering process. The release behavior of copper exhibited a leveling effect upon additional laundering cycles. This may be the result of the complete or almost complete removal of the surface-bound nanoparticles from the fabric.

Figure 11A:
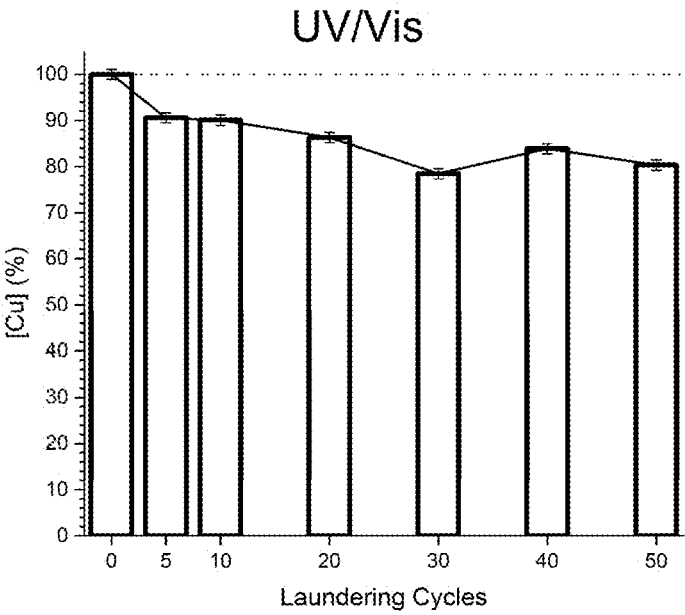
FIG. 11A and FIG. 11B depicts graphs of the percentage copper content remaining in $Cu_2ONP$-cotton fabrics after consecutive laundering cycles.
Figure 11B:
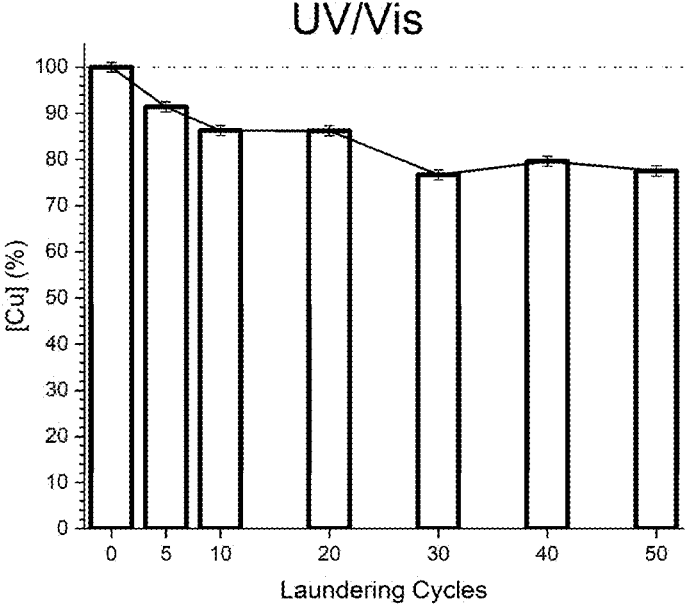

As seen in FIG. 10, examination of the λmax across sequential launderings revealed a blueshift in the peak wavelength from 320 nm at 0 cycles to a lower wavelength of 310 nm after 5 cycles or more. This blueshift in wavelength was attributed to small changes in the surface chemistry of the Cu$_2$O nanoparticles during the laundering since, as shown in FIG. 11, there is not a significant difference in copper concentration of fabrics undergoing 30 to 50 laundering cycles. It is possible that the surfactants and salts present in the detergent can partially oxidize the nanoparticle surface from copper (I) to copper (II), consistent with literature values of CuO λmax between 270 and 310 nm.

This example shows that even after subjecting the fabric comprising internally dispersed cuprous oxide nanoparticles to 50 laundering cycles, at least about over 80% of the cuprous oxide nanoparticles remained in the fabric.

Example 4

Antibacterial and Antifungal Testing

The ability of fabrics comprising internally dispersed cuprous oxide nanoparticles to retain antibacterial and antifungal properties, even after 50 laundering cycles was studied.

Since Cu$_2$ONPs are known to exhibit bactericidal and fungicidal properties, the antibacterial and antifungal properties of Cu$_2$ONP-cotton fabric laundered for 50 cycles was further studied against *Staphylococcus aureus* and *Aspergillus niger*, respectively.

Antibacterial and antifungal properties of washed, copper-treated cotton fabrics against Gram-positive bacterium *Staphylococcus aureus* ATCC 6538 and fungus *Aspergillus niger* ATCC 6275 were tested at Microchem Laboratory (Round Rock, Texas, USA) following the AATCC test method 100-2007: "Assessment of Antibacterial Finishes on Textile Materials" and AATCC test method 30 Test III: "Antifungal Activity, Assessment on Textile Materials: Agar Plate, *Aspergillus niger*", respectively. A percent reduction of bacterial growth was calculated using the following equation:

$$\text{percent reduction } (\%) = \frac{B - A}{B} \times 100 \qquad (2)$$

where A is the number of viable test bacteria on the cotton fabric control sample immediately after inoculation and B is the number of viable test bacteria on the treated cotton fabric test sample after the contact time (24 hours).

Copper nanomaterials have been long used for their remarkable antimicrobial properties in commercial goods. One limitation to these antimicrobial agents when applied to commercial textiles is reduced efficacy after continuous use and laundering cycles. The Cu$_2$ONP-cotton fabric was tested after 50 laundering cycles according to the AATCC test method 100-2007 using gram-positive *Staphylococcus aureus*. The Cu$_2$ONP-cotton fabric exhibited 99.995% inhibition against gram-positive bacteria *Staphylococcus aureus* after just 24 hours, with $10^6$ fewer colony forming units compared to control cotton at time zero. Compared to the results obtained with Cu$_2$O nanoparticles externally applied to cotton fabrics that showed 65% inhibition after 50 laundering cycles (Sharma P., et al., 2019, "Green synthesis and characterization of copper nanoparticles by *Tinospora cardifolia* to produce nature-friendly copper nano-coated fabric and their antimicrobial evaluation," J. Microbiol. Methods 160:107-116, doi:10.1016/j.mimet.2019.03.007). And, with the results obtained for internally formed copper oxide nanoparticles within a thiol-conjugated cotton fabric that exhibited a reduction in antibacterial activity of less than about 99% after just 10 laundering cycles in non-ionic detergent (Gouda M, et al., 2015, "Preparation and Characterization of Some Nanometal Oxides Using Microwave Technique and Their Application to Cotton Fabrics," J. Nanomater. 2015:1-9. doi:10.1155/2015/586904). This superior antibacterial activity of the Cu$_2$ONP-cotton fabric can be attributed to the internally-formed Cu$_2$ONPs. Compared to the externally-applied Cu$_2$O nanoparticles, which are easily detached during laundering resulting in a decreased antibacterial activity, the internally formed Cu$_2$ONPs are sterically trapped in the cotton fabric and resist mechanical detachment. These trapped Cu$_2$ONPs therefore release bactericidal Cu$^+$ ions in a controlled manner. The antifungal activity of the Cu$_2$ONP-cotton fabric was also tested using AATCC test method 30 Test III using fungus *Aspergillus niger*. After 50 laundering cycles the Cu$_2$ONP-cotton fabric inhibited all fungal growth for at least 7 days even in a growth promoting environment. This widespread antimicrobial activity emphasizes the application and utility of the $Cu_2ONP$-cotton fabric to a multitude of commercial and health-related products.

This example shows that even after 50 laundering cycles, fabrics comprising internally dispersed cuprous oxide nanoparticles of the invention inhibited gram-positive bacteria and fungus.

We claim:

1. A treated cellulosic fiber comprising internally dispersed cuprous oxide nanoparticles, wherein the cellulosic fiber has a microfibrillar crystalline structure with unidirectionally aligned microfibrils, and the cuprous oxide nanoparticles are directly incorporated to the cellulosic fiber microfibrillar crystalline structure and are irregular in shape and size; and wherein the only difference between the cellulose microfibrillar crystalline structure of the treated fiber and the fiber prior to cuprous oxide incorporation is the presence of the cuprous oxide nanoparticles incorporated to the microfibrillar crystalline structure.

2. The treated cellulosic fiber of claim 1, wherein the treated cellulosic fiber is from cotton, flax, hemp, jute, ramie, pineapple leaf, or abaca.

3. The treated cellulosic fiber of claim 2, wherein the cotton is greige cotton, scoured cotton, or scoured and bleached cotton.

4. The treated cellulosic fiber of claim 1, wherein the internally dispersed cuprous oxide nanoparticles have a median Feret diameter of about 5 nm to about 100 nm.

5. The treated cellulosic fiber of claim 1, wherein the concentration of internally dispersed cuprous oxide nanoparticles in the treated fiber is at least about 0.001 mg/kg.

6. The treated cellulosic fiber of claim 1, wherein at least about 20% of the cuprous oxide nanoparticles remain internally dispersed in the treated fiber after at least about 5 laundering cycles.

7. The treated cellulosic fiber of claim 1, wherein the treated cellulosic fiber inhibits at least one of odor, microbial growth, bacterial growth, viral growth, or fungal growth.

8. An article comprising at least one treated cellulosic fiber of claim 1.

9. The article of claim 8, wherein the article is at least one of antimicrobial, antibacterial, anti-odor, anti-viral, or anti-fungal.

10. The article of claim 8, wherein the article is a yarn, a thread, a twine, a rope, a cloth, a woven fabric, a knitted fabric, a film-based composite, a nonwoven fabric, or a final article.

11. The final article of claim 10, wherein the final article comprises all or part of athletic wear, an undergarment, military wear, a medical textile, or a functional barrier.

12. The final article of claim 11, wherein the medical textile is a curtain, a bedding, a surgical arena fabric, a personnel protective garment, a wound or non-wound patient dressing, a bandage, a gauze, a packing, or a cleaning material.

13. The final article of claim 10, wherein the final article is all or part of an antimicrobial, antibacterial, anti-odor, anti-viral, or anti-fungal packaging.

14. The final article of claim 13, wherein the antimicrobial, antibacterial, anti-odor, anti-viral, or anti-fungal packaging is an agricultural or food packaging.

15. A method for preparing a treated cellulosic fiber comprising internally dispersed cuprous oxide nanoparticles, the method comprising:

immersing a cellulosic fiber having a microfibrillar crystalline structure with unidirectionally aligned microfibrils in a solution comprising a copper (II) precursor and a base to prepare a $[Cu(OH)_4]^{2-}$ copper complex that diffuses through the interior of the cellulosic fiber microfibrillar crystalline structure;

transferring the cellulosic fiber with the diffused $[Cu(OH)_4]^{2-}$ copper complex to water to produce a cellulosic fiber comprising $Cu(OH)_2$ incorporated to the cellulosic fiber microfibrillar crystalline structure; and allowing the cellulosic fiber comprising $Cu(OH)_2$ to dry, to prepare a treated cellulosic fiber comprising internally dispersed cuprous oxide nanoparticles of irregular shape and size incorporated to the fiber microfibrillar structure; wherein the only difference between the cellulose fiber microfibrillar crystalline structure of the treated fiber and the fiber prior to immersion in the solution comprising the copper (II) precursor is the presence of internally dispersed cuprous oxide nanoparticles.

16. The method of claim 15, wherein the copper (II) precursor is copper (II) sulfate, copper 2-ethylhexanoate, copper acetate triarsenite, copper acetate, copper acetylacetonate, copper acetylide, copper arsenate, copper arsenite, copper aspirinate, copper azide, copper benzoate, copper bromide, copper carbonate, copper carbonate hydroxide, copper chlorate, copper chloride, copper chromate, copper chromite, copper cyanide, copper cyanurate, copper cyclohexanebutyrate, copper fluoride, copper gluconate, copper glycinate, copper hexafluoroacetylacetonate, copper hydride, copper hydroxide, copper iodide, copper nitrate, copper nitrite, copper oxide, copper perchlorate, copper peroxide, copper phosphate, copper phosphide, copper pyrophosphate, copper selenite, copper sulfate pentahydrate, copper sulfate, copper sulfide, copper tartrate, copper t-butoxide, copper tetraamine, copper tetrafluoroborate, copper thiocyanate, copper thiophene-2-carboxylate, copper triflate, copper trifluoroacetate, copper trifluoroacetylacetonate, copper usnate, or a hydrate thereof.

17. The method of claim 15, wherein the base is a hydroxide, a carbonate, or other organic base or inorganic base.

18. The method of claim 15, wherein the cellulosic fiber is cotton, flax, hemp, jute, ramie, pineapple leaf, or abaca.

19. The method of claim 15, wherein the water is at about room temperature.

* * * * *